US009511122B2

(12) United States Patent
Rasmussen et al.

(10) Patent No.: US 9,511,122 B2
(45) Date of Patent: Dec. 6, 2016

(54) DRY GROWTH HORMONE COMPOSITION TRANSIENTLY LINKED TO A POLYMER CARRIER

(75) Inventors: Grethe Nørskov Rasmussen, Farum (DK); Susanne Kindermann, Liestal (CH); Harald Rau, Dossenheim (DE); Thomas Wegge, Heidelberg (DE)

(73) Assignee: Ascendis Pharma Growth Disorders Division A/S, Hellerup (DK)

( * ) Notice: Subject to any disclaimer, the term of this patent is extended or adjusted under 35 U.S.C. 154(b) by 0 days.

(21) Appl. No.: 13/515,621

(22) PCT Filed: Dec. 15, 2010

(86) PCT No.: PCT/EP2010/069710
§ 371 (c)(1),
(2), (4) Date: Aug. 28, 2012

(87) PCT Pub. No.: WO2011/073234
PCT Pub. Date: Jun. 23, 2011

(65) Prior Publication Data
US 2012/0322721 A1 Dec. 20, 2012

(30) Foreign Application Priority Data
Dec. 15, 2009 (EP) .................................... 09179335

(51) Int. Cl.
*A61K 38/27* (2006.01)
*A61K 9/19* (2006.01)
*A61K 9/00* (2006.01)
*A61K 47/48* (2006.01)

(52) U.S. Cl.
CPC ............. *A61K 38/27* (2013.01); *A61K 9/0019* (2013.01); *A61K 9/19* (2013.01); *A61K 47/48215* (2013.01)

(58) Field of Classification Search
CPC .................................. A61K 38/27; A61K 38/00
See application file for complete search history.

(56) References Cited

U.S. PATENT DOCUMENTS

| 4,179,337 | A | 12/1979 | Davis et al. |
| 5,073,627 | A | 12/1991 | Curtis et al. |
| 5,171,220 | A * | 12/1992 | Morimoto ....................... 604/88 |
| 5,472,706 | A | 12/1995 | Friedman et al. |
| 5,478,925 | A | 12/1995 | Wallach et al. |
| 5,645,010 | A | 7/1997 | Lundström |
| 5,971,953 | A * | 10/1999 | Bachynsky ..................... 604/90 |
| 6,284,282 | B1 * | 9/2001 | Maa et al. ..................... 424/499 |
| 7,879,588 | B2 | 2/2011 | Vetter et al. |
| 7,968,085 | B2 | 6/2011 | Hersel et al. |
| 2006/0135427 | A1 | 6/2006 | Hays et al. |
| 2006/0257479 | A1 | 11/2006 | Jensen et al. |
| 2006/0275252 | A1 * | 12/2006 | Harris et al. .............. 424/78.27 |
| 2008/0063727 | A1 | 3/2008 | Kim et al. |
| 2008/0113914 | A1 * | 5/2008 | Hays et al. ..................... 514/12 |
| 2008/0241102 | A1 | 10/2008 | Hersel et al. |
| 2010/0291021 | A1 | 11/2010 | Vetter et al. |
| 2011/0009315 | A1 | 1/2011 | Hersel et al. |
| 2011/0053848 | A1 | 3/2011 | Cleemann et al. |
| 2011/0112021 | A1 | 5/2011 | Rau et al. |
| 2011/0172390 | A1 | 7/2011 | Vetter et al. |
| 2011/0223230 | A1 | 9/2011 | Hersel et al. |
| 2012/0058084 | A1 | 3/2012 | Rau et al. |
| 2012/0156259 | A1 | 6/2012 | Rau et al. |
| 2012/0156260 | A1 | 6/2012 | Rau et al. |

FOREIGN PATENT DOCUMENTS

| EP | 0211257 | 2/1987 |
| EP | 2113256 | 11/2009 |
| EP | 2119726 | 11/2009 |
| RU | 2229288 C2 | 5/2004 |
| WO | WO 94/10308 | 5/1994 |
| WO | WO-9704801 A1 | 2/1997 |
| WO | WO 99/30727 | 6/1999 |
| WO | WO 01/47562 | 7/2001 |
| WO | WO 01/78683 | 10/2001 |
| WO | WO 02/083180 | 10/2002 |
| WO | WO 02/089789 | 11/2002 |
| WO | WO 03/044056 | 11/2003 |
| WO | WO 2004/019993 | 3/2004 |
| WO | WO 2004/043493 | 5/2004 |
| WO | WO 2005/034909 | 4/2005 |
| WO | WO 2005/079838 | 9/2005 |
| WO | WO 2005/099768 | 10/2005 |
| WO | WO 2006/003014 | 1/2006 |
| WO | WO 2006/071840 | 7/2006 |

(Continued)

OTHER PUBLICATIONS

Pfizer, "Highlights of prescribing information", 2008, document pp. 1-24; obtained from http://www.accessdata.fda.gov/scripts/cder/drugsatfda/index.cfm.*
Kumar et al., "Effect of trehalose on protein structure", Protein Science, pp. 24-36; 2009.*
Wolf et al., "Growth Hormone and Insulin Reverse Net Whole Body and Skeletal Muscle Protein Catabolism in Cancer Patients", Annals of Surgery, 1992, pp. 280-288.*
Genentech Inc, "Nutropin AQ®", 2004, pp. 1-27; obtained from http://www.accessdata.fda.gov/drugsatfda_docs/label/2005/020522s021,022lbl.pdf).*
Kalia et al., "Hydrolytic Stability of Hydrazones and Oximes", Angew. Chem. Int. Ed., 2008, pp. 7523-7526.*
Wang, "Lyophilization and development of solid protein pharmaceuticals", International Journal of Pharmaceutics, 2002, pp. 1-60.*
Graham et al., "AAS, growth hormone and insulin abuse: psychological and neuroendocrine effects", Therapeutics and Clinical Risk Management, 2008; pp. 587-597.*

(Continued)

*Primary Examiner* — Lianko Garyu
(74) *Attorney, Agent, or Firm* — Frommer Lawrence & Haug LLP

(57) ABSTRACT

The present invention relates to dry compositions of rhGH polymer prodrug containing a lyoprotectant and, optionally, one or more than one excipient. Such compositions are stable for at least 1 year, when stored at 2-8° C. The invention further relates to methods of manufacturing said compositions, containers comprising such composition as well as a kit of parts.

36 Claims, 1 Drawing Sheet

(56) References Cited

FOREIGN PATENT DOCUMENTS

| WO | WO 2006/102659 | | 9/2006 |
|---|---|---|---|
| WO | WO 2006/136586 | | 12/2006 |
| WO | WO 2007/025988 | | 3/2007 |
| WO | WO 2007/075534 | | 7/2007 |
| WO | WO 2007/114881 | | 10/2007 |
| WO | WO 2008084237 | A2 * | 7/2008 |
| WO | WO 2008/112155 | | 9/2008 |
| WO | WO 2009/095479 | | 8/2009 |
| WO | WO 2009/133137 | | 11/2009 |
| WO | WO 2009133137 | A2 * | 11/2009 |

OTHER PUBLICATIONS

Kidder et al., "Effects of Growth Hormone and Low Dose Estrogen on Bone Growth and Turnover in Long Bones of Hypophysectomized Rats", Calcif Tissue Int, 1997, pp. 327-335.*

Semlaty et al., "Properties and Formulation of Oral Drug Delivery Systems of Protein and Peptides", Indian Journal of Pharmaceutical Sciences, 2007, pp. 741-747.*

Garman et al., "The preparation and properties of novel reversible polymer-protein conjugates", FEBS Lett., Nov. 1987, vol. 223, No. 2, 361-365, Elsevier Science Publishers B.V.

Antczak et al., "A New Aciviein Prodrug Designed for Tumor-targeted Delivery", Bioorganic & Medicinal Chemistry, 2001, 9, 2843-2848, Elsevier Ltd.

Bowie et al., "Deciphering the Message in Protein Sequences: Tolerance to Amino Acid Substitutions", Science, Mar. 1990, 247, 1306-1310, Highwire Press.

Clark et al., "Long-acting Growth hormones Produced by Conjugation with Polyetylene Glycol", J. Bio. Chem., 1996, 271:36, 21969-21977, American Society for Biochemistry and Molecular Biology, Inc.

Garman et al., "The preparation and properties of novel reversible polymer-protein conjugates: 2-ω-Methoxypolyethylene (5000) glyeoxymethylene-3-methylmaleyl conjugates of plasminogen activators", Federation or European Biochemical Societies, 1987, 223:2, 361-365, Elsevier Science Publishers B.V.

Greenwald et al., "Drug Delivery Systems Employing 1,4- or 1,6-Elimination: Poly(ethylene glycol) Prodrugs of Amine-Containing Compounds", J. Med. Chem., 1999, 42, 3657-3667, American Chemical Society.

Greenwald et at., "Drug Delivery Systems Based on Trimethyl Lock Lactonization: Poly(ethylene glycol) Prodrugs of Amino-Containing Compounds", J. Med. Chem., 2000, 43, 475-487, American Chemical Society.

Greenwald et al., "A New Aliphatic Amino Prodrug System for the Delivery of Small Molecules and Proteins Utilizing Novel PEG Derivatives", J. Med. Chem. 2004, 726-734, 47, American Chemical Society.

Grigorian et al., "Extraordinarily stable disulfide-linked homodimer of human growth hormone", Protein Science, 2005, 902-913, 14, Cold Spring Harbor Laboratory Press.

Lee et al., "Targeted Enzyme-Responsive Drug Carriers: Studies on the Delivery of a Combination of Drugs", Angew. Chem., 2004, 1707-1710, 116, Wiley-VCH Verlag GmbH &Co., Weinheim.

Lee et al., "Drug Delivery Systems Employing 1,6-Elimination: Releasable Poly(ethylene glycol) Conjugates of Proteins", Bioconjugate Chem., 2001, 163-169, 12, American Chemical Society.

Ron et al., "Expression of Biologically Active Recombinant Keratinocyte Growth Factor",Journal of Biological Chemistry, 1993, 2984-2988, 268 (4), American Society for Biochemistry and MolecularBiology.

Shabat et al., "Chemical Adaptor Systems", Chem. Eur. J., 2004, 2626-2634, 10, Wiley-VCH Verlag GmbH &Co., Weinheim.

Tsubery et al., "Prolonging the Action of Protein and Peptide Drugs by a Novel Approach of Reversible Polyethylene Glycol Modification", Journal of Biological Chemistry, 2004, 38118-38124, 279 (37), The American Society for Biochemistry and Molecular Biology.

V.G. Belikov, "Farmazevtit'cheskaya Khimia (Pharmaceutical chemistry), Part 1, Moscov Vysshaya shkola", 1993, pp. 43-45.

* cited by examiner

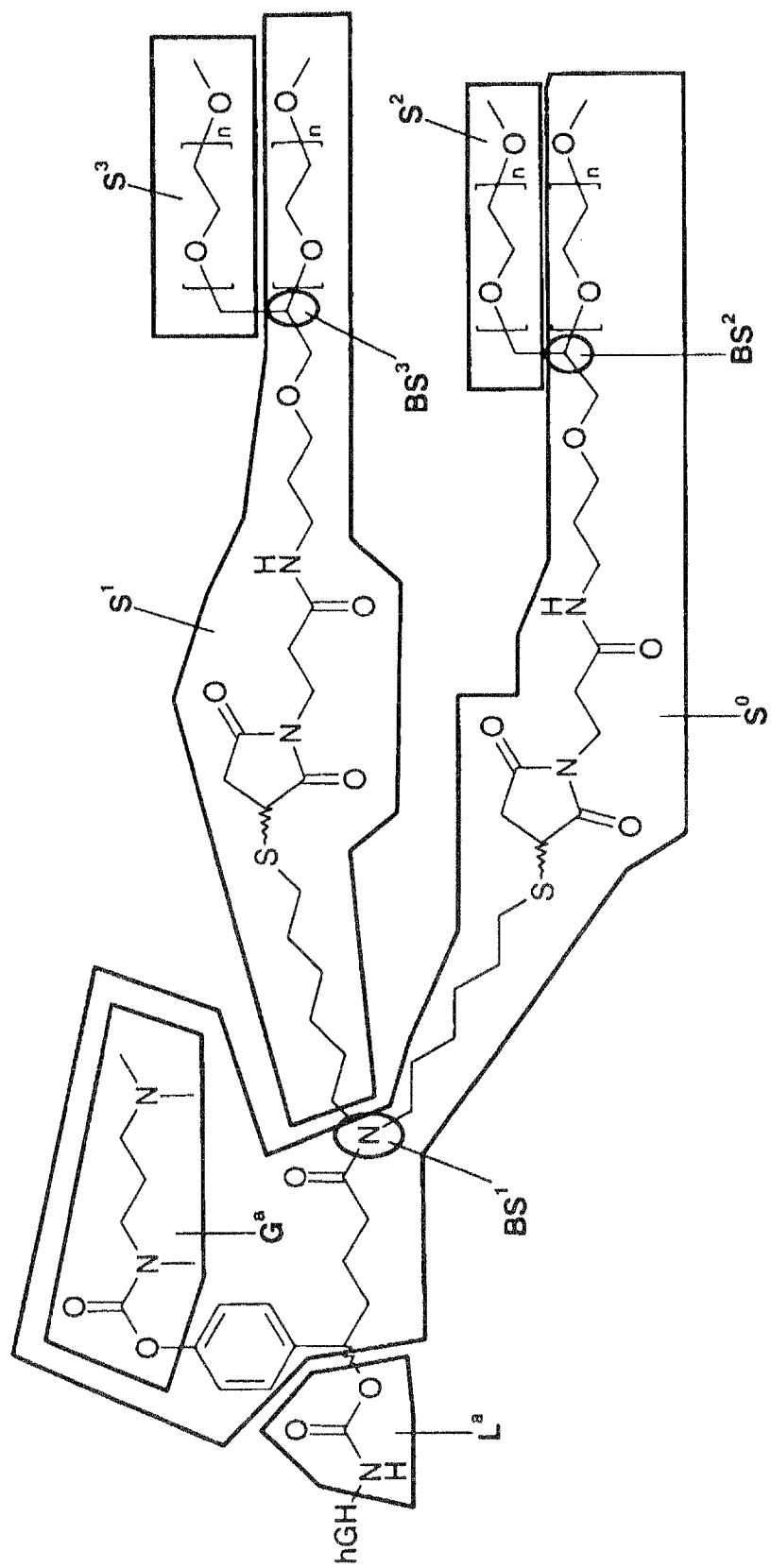

SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

```
<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190
```

DRY GROWTH HORMONE COMPOSITION TRANSIENTLY LINKED TO A POLYMER CARRIER

The present application claims priority from PCT Patent Application No. PCT/EP2010/069710 filed on Dec. 15, 2010, which claims priority from European Patent Application No. EP 09179335.6 filed on Dec. 15, 2009, the disclosures of which are incorporated herein by reference in their entirety.

BACKGROUND OF THE INVENTION

1. Field of the Invention

The present invention relates to dry compositions of rhGH polymer prodrugs, methods for their manufacture as well as containers and kits of parts comprising said compositions.

It is noted that citation or identification of any document in this application is not an admission that such document is available as prior art to the present invention.

Growth hormone (GH) is a hormone that stimulates growth and cell reproduction in humans and other animals. It is a 191-amino acid, single-chain polypeptide hormone which is synthesized, stored, and secreted by the somatotroph cells within the lateral wings of the anterior pituitary gland. The hormone is also known as somatotropin when referring to human growth hormone (hGH) produced by recombinant DNA technology, and is abbreviated "rhGH".

Growth hormone has a variety of functions in the body, the most noticeable of which is the increase of height throughout childhood, and there are several diseases which can be treated through the therapeutic use of GH.

Growth hormone deficiency is caused by insufficient production of growth hormone which causes various negative effects. During infancy and childhood the most prominent feature is growth failure, resulting in short stature, whereas in adults it causes diminished lean body mass, poor bone density and other physical and psychological effects. The standard treatment of growth hormone deficiency is daily injections with recombinant human growth hormone (rhGH) under the skin or into the muscle.

To free the pediatric patient group from the burden of daily injections, long-acting growth hormone compositions are intended to provide therapy of growth hormone deficiency in children. Various compositions of long-acting or sustained release human growth hormone are described. Growth hormone depots of the first generation were based on slow-release compositions of the human growth hormone in highly viscous liquid such as sucrose acetate isobutyrate (WO 01/78683, Genentech) or biodegradable PLGA (polylactide/polyglycolide) gel. U.S. Pat. No. 5,645,010, Alkermes, describes a composition of zinc-complexed hGH in PLGA. A corresponding marketed product (Nutropin Depot) was offered as single-dose injectable composition. For various reasons, Nutropin Depot did not show significant market uptake and was discontinued.

More recent polymer-based compositions employed hyaluronic acid instead of PLGA (US 2008/0063727, LG Life Sciences). Other developments focused on PEG conjugates of growth hormone with the goal of extending both the absorption phase from the subcutaneous tissue after injection as well as the terminal half-life of the circulating conjugate (U.S. Pat. No. 4,179,337 describes the PEGylation of somatropin, as does WO 03/044056, Pharmacia, and WO 06/102659, Nektar).

Nevertheless, only few details are available on how to formulate PEGylated growth hormone. As PEG itself is a highly viscous material, corresponding protein conjugates carrying high molecular weight PEG chains also exhibit strongly enhanced viscosity as compared to the unmodified protein. This situation is even more pronounced as it is desirable to provide for sufficient material for a less frequent than daily dosage while at the same time seeking to minimize the injection volume. Consequently, compositions of long-acting PEGylated growth hormone are much more concentrated and viscous than the existing once-daily compositions of unmodified growth hormone.

WO 2006/071840, Ambrx, details compositions of PEGylated growth hormone variants incorporating non-natural amino acids. WO 2007/025988, Novo, describes compositions containg growth hormone and PEG through an oxime bond. US 26/257479, Novo, details compositions of PEG growth hormone conjugates in PLGA. An expansion of the scope of PEGylation was recently introduced by the use of reversible linkers in a prodrug approach. A PEGylated prodrug of hGH exhibits significantly reduced bioactivity of the PEGylated conjugate but exhibits full uncompromised bioactivity of the free growth hormone released from the conjugate.

Compositions of such hGH prodrugs do not only have to take into account the viscosity introduced by the PEG component, but also have to provide for sufficient prodrug stability to avoid premature hGH release during storage. In case the reversible linkage between the PEG moiety and the drug is degraded during storage, the concentration of readily available drug is increased, which leads to the risk of overdosage. In addition, any drug released during storage is subject to rapid renal clearance upon application to a patient and, as a consequence, the time for which the long-acting composition provides therapeutically relevant amounts of drug is reduced. This poses the risk of unmet medical needs.

Furthermore, it is known that rhGH will undergo decomposition reactions under storage conditions, leading to impurities of the corresponding composition. It is therefore mandatory to identify suitable rhGH polymer prodrug compositions, wherein the rhGH will exhibit an acceptable impurity profile.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

It is therefore of paramount interest to develop compositions of hGH polymer prodrugs that ensure the stability of the rhGH polymer prodrug compound.

Furthermore, it is desirable to provide for single-dose as well as multiple-dose compositions of such hGH polymer prodrugs.

Thus an object of the present invention is to provide such compositions.

The object is achieved by a dry composition comprising a therapeutically effective amount of a rhGH polymer prodrug and one or more lyoprotectants and optionally one or more pharmaceutically acceptable excipients, wherein the growth hormone is transiently linked to a polymer carrier.

In the context of the present invention terms and phrases are used as follows.

Since the recombinant human GH is identical in sequence to natural human GH, the term recombinant human growth hormone (rhGH) relates herein also to so-called biogenerics equivalents. Thus, the terms rhGH and hGH can be used synonymously within the meaning of the present invention.

As known to the person skilled in the art, it is today routine work to make e.g. minor amino changes of a biologics of interest (herein: GH) without significantly affecting the activity of the biologics.

Besides recombinant human and biogenerics, the term recombinant human growth hormone relates herein also to all possible rhGH polypeptides.

A precise description of possible rhGH polypeptides is given in WO-A 2005/079838 from the Pharmacia Corporation provided on page 15, paragraph 0043 till and including paragraph 0053.

The term "hGH polypeptide or hGH protein", when used herein, encompasses all hGH polypeptides, preferably from mammalian species, more preferably from human and murine species, as well as their variants, analogs, orthologs, homologs, and derivatives, and fragments thereof that are characterized by promoting growth in the growing phase and in maintaining normal body composition, anabolism, and lipid metabolism. Optionally, the term "hGH polypeptide or hGH protein" further includes hGH with one or more additional amino acid residues compared to naturally occurring hGH variants, whereas these additional amino acids residues may either at the N-terminus, C-terminus and/or internally. It is understood that the term "hGH polypeptide or hGH protein" also refers to hGH variants with any combination of additional, deleted or exchanged amino acid residues.

Preferably, the term "hGH polypeptide or hGH protein", when used herein, encompasses all hGH polypeptides, preferably from mammalian species, more preferably from human and murine species, as well as their variants, analogs, orthologs, homologs, and derivatives, and fragments thereof that are characterized by promoting growth in the growing phase and in maintaining normal body composition, anabolism, and lipid metabolism.

More preferably, the hGH polypeptide or hGH protein is at least 95% identical to the sequence using the 1-letter code for amino acids according to IUPAC-IUB known to the person skilled in the art given below:

```
                                              (SEQ ID NO: 1)
FPTIPLSRLFDNAMLRAHRLHQLAFDTYQEFEEAYIPKEQKYSFLQN

PQTSLCFSESIPTPSNREETQQKSNLELLRISLLLIQSWLEPVQFLRSV

FANSLVYGASDSNVYDLLKDLEEGIQTLMGRLEDGSPRTGQIFKQTYSK

FDTNSHNDDALLKNYGLLYCFRKDMDKVETFLRIVQCRSVEGSCGF
```

The term "hGH polypeptide or protein" preferably refers to the 22 kDa hGH polypeptide having a sequence as disclosed in A. L. Grigorian et al., Protein Science (2005), 14, 902-913 as well as its variants, homologs and derivatives exhibiting essentially the same biological activity (promoting growth in the growing phase and in maintaining normal body composition, anabolism, and lipid metabolism). More preferably, the term "hGH polypeptide or protein" refers to the polypeptide having exactly the abovementioned sequence.

The term "hGH polypeptide variants", as used herein, refers to polypeptides from the same species but differing from a reference hGH polypeptide. Generally, differences are limited so that the amino acid sequences of the reference and the variant are closely similar overall and, in many regions, identical. Preferably; hGH polypeptides are at least 70%, 80%, 90%, 95%, 96%, 97%, 98% or 99% identical to a reference hGH polypeptide, preferably the hGH polypeptide having a sequence as indicated in A. L. Grigorian et al., Protein Science (2005), 14, 902-913. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein.

Such hGH polypeptide variants may be naturally occurring variants, such as naturally occurring allelic variants encoded by one of several alternate forms of a hGH occupying a given locus on a chromosome of an organism, or isoforms encoded by naturally occurring splice variants originating from a single primary transcript. Alternatively, a hGH polypeptide variant may be a variant that is not known to occur naturally and that can be made using art-known mutagenesis techniques.

It is known in the art that one or more amino acids may be deleted from the N-terminus or C-terminus of a bioactive peptide or protein without substantial loss of biological function (see for instance, Ron et al., (1993), Biol. Chem., 268 2984-2988 which disclosure is hereby incorporated by reference in its entirety).

It also will be recognized by one of ordinary skill in the art that some amino acid sequences of hGH polypeptides can be varied without significant effect of the structure or function of the protein. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, hereby incorporated by reference in its entirety, wherein the authors indicate that there are two main approaches for studying the tolerance of an amino acid sequence to change.

The first method relies on the process of evolution, in which mutations are either accepted or rejected by natural selection. The second approach uses genetic engineering to introduce amino acid changes at specific positions of a cloned hGH and selections or screens to identify sequences that maintain functionality. These studies have revealed that proteins are surprisingly tolerant of amino acid substitutions.

The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., (1990) supra, and the references cited therein.

Typically seen as conservative substitutions are the replacements, one for another, among the aliphatic amino acids Ala, Val, Leu and Phe interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. In addition, the following groups of amino acids generally represent equivalent changes: (1) Ala, Pro, Gly, Glu, Asp, Gln, Asn, Ser, Thr; (2) Cys, Ser, Tyr, Thr; (3) Val, He, Leu, Met, Ala, Phe; (4) Lys, Arg, His; (5) Phe, Tyr, Trp, His.

The term hGH polypeptide also encompasses all hGH polypeptides encoded by hGH analogs, orthologs, and/or species homologues. As used herein, the term "hGH analogs" refers to hGHs of different and unrelated organisms which perform the same functions in each organism but which did not originate from an ancestral structure that the organisms' ancestors had in common. Instead, analogous hGHs arose separately and then later evolved to perform the same function (or similar functions). In other words, analogous hGH polypeptides are polypeptides with quite different amino acid sequences but that perform the same biological activity, namely promoting growth in the growing phase and in maintaining normal body composition, anabolism, and lipid metabolism. As used herein, the term "hGH orthologs" refers to hGHs within two different species which sequences are related to each other via a common homologous hGH in an ancestral species but which have evolved to become different from each other. As used herein, the term "hGH homologs" refers to hGHs of different organisms which perform the same functions in each organism and which originate from an ancestral structure that the organisms' ancestors had in common. In other words, homologous hGH polypeptides are polypeptides with quite similar amino acid sequences that perform the same biological activity, namely promoting growth in the growing phase and in maintaining normal body composition, anabolism, and lipid metabolism. Preferably, hGH polypeptide homologs may be defined as polypeptides exhibiting at least 40%, 50%, 60%, 70%, 80%, 90%, 95%, 96%, 97%, 98% or 99% identity to a reference hGH polypeptide, preferably the hGH polypeptide having a sequence as mentioned above.

Thus, a hGH polypeptide may be, for example: (i) one in which one or more of the amino acid residues are substituted with a conserved or non-conserved amino acid residue (preferably a conserved amino acid residue) and such substituted amino acid residue mayor may not be one encoded by the genetic code: or (ii) one in which one or more of the amino acid residues includes a substituent group: or (iii) one in which the hGH polypeptide is fused with another compound, such as a compound to increase the half-life of the polypeptide (for example, polyethylene glycol): or (iv) one in which the additional amino acids are fused to the above form of the polypeptide, such as an IgG Fc fusion region peptide or leader or secretory sequence or a sequence which is employed for purification of the above form of the polypeptide or a pro-protein sequence.

hGH polypeptides may be monomers or multimers. Multimers may be dimers, trimers, tetramers or multimers comprising at least five monomeric polypeptide units. Multimers may also be homodimers or heterodimers. Multimers may be the result of hydrophobic, hydrophilic, ionic and/or covalent associations and/or may be indirectly linked, by for example, liposome formation. In one example, covalent associations are between the heterologous sequences contained in a fusion protein containing a hGH polypeptide or fragment thereof (see, e.g., U.S. Pat. No. 5,478,925, which disclosure is hereby incorporated by reference in its entirety). In another example, a hGH polypeptide or fragment thereof is joined to one or more polypeptides that may be either hGH polypeptides or heterologous polypeptides through peptide linkers such as those described in U.S. Pat. No. 5,073,627 (hereby incorporated by reference).

Another method for preparing multimer hGH polypeptides involves use of hGH polypeptides fused to a leucine zipper or isoleucine zipper polypeptide sequence known to promote multimerization of the proteins in which they are found using techniques known to those skilled in the art, including the teachings of WO 94/10308. In another example, hGH polypeptides may be associated by interactions between Flag® polypeptide sequence contained in fusion hGH polypeptides containing Flag® polypeptide sequence. hGH multimers may also be generated using chemical techniques known in the art such as cross-linking using linker molecules and linker molecule length optimization techniques known in the art (see, e.g., U.S. Pat. No. 5,478,925), techniques known in the art to form one or more inter-molecule cross-links between the cysteine residues located within the sequence of the polypeptides desired to be contained in the multimer (see, e.g., U.S. Pat. No. 5,478,925, addition of cysteine or biotin to the C terminus or N-terminus of hGH polypeptide and techniques to generate multimers containing one or more of these modified polypeptides (see, e.g., U.S. Pat. No. 5,478,925), or any of the 30 techniques to generate liposomes containing hGH multimers (see, e.g., U.S. Pat. No. 5,478,925), which disclosures are incorporated by reference in their entireties.

As used herein, the term "hGH polypeptide fragment" refers to any peptide or polypeptide comprising a contiguous span of a part of the amino acid sequence of an hGH polypeptide, preferably the polypeptide having the above-mentioned sequence, i.e. it refers to hGH polypeptides having one or more deletions of at least one amino acid residue at the N-terminus, C-terminus and/or internally, when compared to naturally occurring variants.

It is well known that rhGH or its variants, conjugates or derivatives may undergo decomposition reactions which may lead to impurities, such as:

Succinimide and isoaspartate degradation products (impurities): Formation of isoaspartyl peptide bonds is one of the most common forms of non-enzymatic degradation of peptides and proteins under mild conditions. For hGH, the primary site of succinimide formation and subsequent hydrolysis to iso-aspartate and aspartate is ASP130.

Degradation products (impurities) resulting from deamidation: Under mild conditions, the primary deamidation sites of hGH are ASN149 and ASN152.

Degradation products (impurities) resulting from oxidation: Under mild conditions, the primary oxidation site of hGH is MET14.

To enhance physicochemical or pharmacokinetic properties of a drug, such as rhGH, in vivo, such drug can be conjugated with a carrier. If the drug is transiently bound to a carrier and/or a linker, such systems are commonly assigned as carrier-linked prodrugs. According to the definitions provided by IUPAC (as given under http://www- .chem.qmul.ac.uk/iupac.medchem, accessed on Jul. 22, 2009), a carrier-linked prodrug is a prodrug that contains a temporary linkage of a given active substance with a transient carrier group that produces improved physicochemical or pharmacokinetic properties and that can be easily removed in vivo, usually by a hydrolytic cleavage.

The linkers employed in such carrier-linked prodrugs are transient, meaning that they are non-enzymatically hydrolytically degradable (cleavable) under physiological conditions (aqueous buffer at pH 7.4, 37° C.) with half-lives ranging from, for example, one hour to three months. The terms "transient" and "reversible" are used synonymously.

It is clear to the person skilled in the art that the hGH polymer prodrugs are covalent conjugates, meaning that the hGH moiety is covalently attached to the polymer via the reversible linker moiety.

Preferably, the linkers employed in the hGH polymer prodrugs are traceless, meaning that they release hGH in its free form.

Suitable carriers are polymers and can either be directly conjugated to the linker or via a non-cleavable spacer. The term "hGH polymer prodrug" refers to carrier-linked prodrugs of hGH, wherein the carrier is a polymer.

The term polymer describes a molecule comprised of repeating structural units connected by chemical bonds in a linear, circular, branched, crosslinked or dendrimeric way or a combination thereof, which can be of synthetic or biological origin or a combination of both. Typically, a polymer has a molecular weight of at least 1 kDa.

Polymers are preferably selected from the group consisting of for example, 2-methacryloyl-oxyethyl phosphoyl cholins, hydrogels, PEG-based hydrogels, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), polyethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, mannans, pectins, rhamnogalacturonans, starches, hydroxyalkyl starches, hydroxyethyl starches and other carbohydrate-based polymers, xylans, and copolymers thereof.

The term "PEG" or "pegylation residue" is used herein exemplary for suitable water-soluble polymers characterized by repeating units. Suitable polymers may be selected from the group consisting of polyakloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacry-lates, polymethacrylates, polyorganophosphazenes, polysiloxanes, polyvinylpyrrolidone, polycyanoacrylates, and polyesters. Preferred are polyalkyloxy polymers, especially polyethylene glycol polymers containing at least 10% by weight ethylene oxide units, more preferably at least 25% by weight, even more preferably at least 50% by weight.

"Composition" refers to an intermixture of two or more chemical substances. A pharmaceutical composition comprises the pharmaceutically active moiety, either in its free form or as a prodrug, and pharmaceutically acceptable excipients and/or carriers.

"Dry composition" means that the hGH polymer prodrug composition is provided in a dry form in a container. Suitable methods for drying are spray-drying and lyophilization (freeze-drying). Such dry composition of hGH polymer prodrug has a residual water content of a maximum of 10%, preferably less than 5% and more preferably less than 2% (determined according to Karl Fischer). The preferred method of drying is lyophilization. "Lyophilized composition" means that the hGH polymer prodrug composition was first frozen and subsequently subjected to water reduction by means of reduced pressure. This terminology does not exclude additional drying steps which occur in the manufacturing process prior to filling the composition into the final container.

"Lyophilization" (freeze-drying) is a dehydration process, characterized by freezing a composition and then reducing the surrounding pressure and, optionally, adding heat to allow the frozen water in the composition to sublime directly from the solid phase to gas. Typically, the sublimed water is collected by desublimation.

"Reconstitution" means the addition of a liquid to bring back the original form of a composition, such as a solution.

"Reconstitution solution" refers to the liquid used to reconstitute the dry composition of a rhGH polymer prodrug prior to administration to a patient in need thereof.

"Container" means any container in which the rhGH polymer prodrug composition is comprised and can be stored until reconstitution.

"Stable" and "stability" means that within the indicated storage time the polymer conjugates remain conjugated and do not hydrolyze to a substantial extent and exhibit an acceptable impurity profile relating to rhGH. To be considered stable, the composition contains less than 5% of the drug in its free form and low amounts of rhGH-related impurities, such as ASP130 succinimide and isoaspartate formation, ASN140 and ASN152 deamidation, and MET14 oxidation. Impurities may be quantified as tryptic peptides based on their respective peak area relative to the peak area of the corresponding unmodified tryptic peptide and "low amounts" may correspond to an occurrence of such impurity to an extent of not greater than 20%, preferably not greater than 10%, even more preferably not greater than 5% (per impurity).

"Free form" of a drug refers to the drug in its unmodified, pharmacologically fully active form, e.g. after being released from the polymer conjugate.

"Therapeutically effective amount" means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician. Within the scope of this invention, therapeutically effective amount relates to dosages that aim to achieve therapeutic effect for an extended period of time, i.e. for three days or longer, for instance one week or two weeks.

"Buffer" or "buffering agent" refers to chemical compounds that maintain the pH in a desired range. Physiologically tolerated buffers are, for example, sodium phosphate, succinate, histidine, bicarbonate, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability.

"Excipients" refers to compounds administered together with the therapeutic agent, for example, buffering agents, isotonicity modifiers, preservatives, stabilizers, anti-adsorption agents, oxidation protection agents, or other auxiliary agents. However, in some cases, one excipient may have dual or triple functions.

A "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as monosodium glutamate or histidine or arginine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

Preferably, a "lyoprotectant" is a molecule which, when combined with a protein of interest, significantly prevents or reduces chemical and/or physical instability of the protein upon drying in general and especially during lyophilization and subsequent storage. Exemplary lyoprotectants include sugars, such as sucrose or trehalose; amino acids such as monosodium glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ethylene glycol; propylene glycol; polyethylene glycol; pluronics; hydroxyalkyl starches, e.g. hydroxyethyl starch (HES), and combinations thereof.

The lyoprotectant is preferably added in a "lyoprotecting amount" to the composition before the drying step, which means that, following lyophilization of the protein in the presence of the lyoprotecting amount of the lyoprotectant, the protein essentially retains its physical and chemical stability and integrity upon lyophilization and storage.

"Surfactant" refers to wetting agents that lower the surface tension of a liquid.

"Isotonicity modifiers" refer to compounds which minimize pain that can result from cell damage due to osmotic pressure differences at the injection depot.

The term "stabilizers" refers to compounds used to stabilize the polymer prodrug. Stabilisation is achieved by strengthening of the protein-stabilising forces, by destabilisation of the denatured state, or by direct binding of excipients to the protein.

"Anti-adsorption agents" refers to mainly ionic or non-ionic surfactants or other proteins or soluble polymers used to coat or adsorb competitively to the inner surface of the composition's container Chosen concentration and type of excipient depends on the effect to be avoided but typically a monolayer of surfactant is formed at the interface just above the CMC value.

"Oxidation protection agents" refers to antioxidants such as ascorbic acid, ectoine, glutathione, methionine, monothioglycerol, morin, polyethylenimine (PEI), propyl gallate, vitamin E, chelating agents such as citric acid, EDTA, hexaphosphate, thioglycolic acid.

"Antimicrobial" refers to a chemical substance that kills or inhibits the growth of microorganisms, such as bacteria, fungi, yeasts, protozoans and/or destroys viruses.

"Pharmaceutically acceptable" is meant to encompass any excipient and/or additive, which does not interfere with the effectiveness of the biological activity of the active ingredient and that, is not toxic to the host to which it is administered.

"Sealing a container" means that the container is closed in such way that it is airtight, allowing no gas exchange between the outside and the inside and keeping the content sterile.

BRIEF DESCRIPTION OF THE DRAWINGS

FIG. 1 shows exemplary structure 1 of type (AA1, AAA1), where the at least 5 kDa polymer chain of $S^0$ comprising $G^a$ and $BS^1$ and $BS^2$ is marked as $S^0$; the carbamate group resulting from $L^a$ and the primary amino group of hGH is marked as $L^a$; $BS^1$ comprises the at least 4 kDa polymer chain marked as $S^1$, wherein $S^1$ comprises $BS^3$, which comprises the at least 4 kDa polymer chain marked as $S^3$. $BS^2$ comprises the at least 4 kDa polymer chain marked as $S^2$.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

The compositions of the present invention contain rhGH polymer prodrugs. Preferably, the rhGH polymer prodrugs have the formula shown in (AB)

$$\text{hGH-(NH-L-}S^0)_n \qquad\qquad (AB),$$

wherein n is 2, 3, or 4; preferably 2;

hGH(—NH)$_n$ represents the hGH residue;

each L is a functional group $L^a$, which is self hydrolysable (auto-cleavable) by an auto-cleavage inducing group $G^a$; and each $S^0$ is independently a polymer chain having a molecular weight of at least 5 kDa, wherein $S^0$ is optionally branched by comprising an at least first branching structure $BS^1$, the at least first branching structure $BS^1$ comprising an at least second polymer chain $S^1$ having a molecular weight of at least 4 kDa, wherein at least one of $S^0$, $BS^1$, $S^1$ further comprises the auto-cleavage inducing group $G^a$ and wherein the molecular weight of the prodrug conjugate without the hGH-NH is at least 25 kDa and at most 1000 kDa, preferably at least 25 kDa and at most 500 kDa, even more preferably at least 30 kDa and at most 250 kDa, even more preferably at least 30 kDa and at most 120 kDa, even more preferably at least 40 kDa and at most 100 kDa.

In a preferred embodiment, the polymer is PEG and the total PEG load per growth hormone molecule amounts to at least 25 kDa. Generally, the total PEG load will be less than 1000 kDa. Preferably, the PEG load is at least 25 kDa and at most 500 kDa, even more preferably at least 30 kDa and at most 250 kDa, even more preferably at least 30 kDa and at most 120 kDa, even more preferably at least 40 kDa and at most 100 kDa, even more preferably at least 40 kDa and at most 90 kDa.

PEG may be attached to hGH through one or more anchoring points. In case of one anchoring point, the corresponding PEG in the hGH PEG prodrug monoconjugate will be branched and contains at least 3 chains. In case of more than one anchoring point, such as in a bisconjugate, the corresponding PEG in the hGH. PEG prodrug may be branched or linear. Bisconjugates may contain linear or branched PEG or may contain a mixture of one linear and one branched PEG chain. In case a branched PEG chain is used, there may be one or more branching units.

A branched PEG is a PEG molecule consisting of a branching point connecting two or more PEG chains, to form a molecule with one anchoring point for attachment to growth hormone. This could be two 20 kDa PEG chains joined to form one branched 40 kDa PEG molecule. In the case where the molecule contains two or three branching points, the molecule is referred to 3 and 4 armed PEG, respectively.

In summary and within the restrictions mentioned above, the PEG polymer is not limited to a particular structure and can be linear, branched, or multi-armed (e.g. forked PEG or PEG attached to a polyol core), dendritic, or with degradable linkers.

The PEGylation to native human GH may occur on several lysine groups or on the N-terminal amine (F1) as well described by Clark et al. (reference 2 herein) on page 21973 table III. Highly reactive are positions F1 and LYS-140. Moderately reactive positions are LYS-115, LYS-38, and LYS-70. Poorly reactive are positions LYS-172, LYS-41, LYS-158 and LYS-168. However, PEGylation may occur at any lysine residues of GH and/or at the N-terminal amine.

The rhGH polymer prodrugs of the dry compositions of the present invention are preferably PEGylated at one or more of the lysines selected from the group consisting of Lys158, Lys145, Lys38, Lys140 and Lys70. More preferably, PEGylation of the hGH moiety occurs mainly at positions Lys158, Lys145, Lys38 and Lys140, even more preferably mainly at positions Lys158, Lys145 and Lys38.

Preferably, at least 30% of all growth hormone moieties of the composition of the present invention are PEGylated at position Lys158.

In this context, the phrase "PEGylation occurs mainly at position LysX" means that at least 10% of all rhGH moieties of the rhGH polymer prodrugs are PEGylated at amino acid position X.

In more general terms the PEG used herein in combination with a transient linker may reduce the risk of lipoatrophy by suitable choice of said polymer. However the principles of the present invention also apply to polymers other than PEG. Thus the term PEG is only used herein exemplary for suitable polymers.

Thus, in a preferred embodiment, hGH PEG prodrug is a monoconjugate conjugated with one of its primary amino groups to an auto-cleavable functional group $L^a$ to a polymer chain $S^0$. This polymer chain $S^0$ has a molecular weight of at least 5 kDa and comprises at least one branching structure $BS^1$. The branching structure $BS^1$ comprises a second polymer chain $S^1$, which has a molecular weight of at least 4 kDa.

As outlined above, at least a third polymer chain $S^2$ is required to have a molecular weight of at least 4 kDa. The polymer chain $S^2$ may be a part of $BS^1$ or may be a further branch of $S^0$ or $S^1$ resulting in a further branching structure $BS^2$, which comprises $S^2$.

Optionally, more than 3 polymer chains are present in the prodrug conjugate comprised in the dry compositions of the present invention, e.g. 4, 5, 6, 7, or 8. However each further polymer chain has a molecular weight of at least 4 kDa. The total number of polymer chains is limited by the total weight of the prodrug conjugate being at most 1000 Da (without hGH-NH).

Thus, a preferred embodiment of the rhGH polymer prodrug comprised in the dry composition of the present invention relates to prodrug, wherein at least one of the branching structures $BS^1$, $BS^2$ comprises a further fourth polymer chain $S^3$ having a molecular weight of at least 4 kDa or one of $S^0$, $S^1$, $S^2$ comprises a third branching structure $BS^1$ comprising the at least fourth polymer chain $S^3$ having a molecular weight of at least 4 kDa.

The auto-cleavage inducing group $G^a$, which is necessary for the auto-cleavage of $L^a$ is comprised by one of the branching structures or polymer chains.

Optionally, one of the branching structures serves as group $G^a$ so that the branching structure consists of $G^a$ (instead of comprising said group), which is also encompassed by the term "comprising".

FIG. 1 illustrates the meaning of $L^a$, $G^a$, $S^0$, $S^1$, $S^2$, $S^3$, $BS^1$, $BS^2$ and $BS^3$ using an exemplary hGH polymer prodrug.

The preparation of a prodrug conjugate (AA) normally results in a mixture of conjugates, where several primary amino groups of hGH are conjugated resulting in different mono-conjugated, different hi-conjugated, different tri-conjugated, etc., prodrugs. Corresponding monoconjugated, bisconjugated or trisconjugated hGH PEG prodrugs can be separated by standard methods known in the art, like column chromatography and the like.

In monoconjugates of hGH PEG prodrugs, the at least three polymer chains $S^0$, $S^1$, $S^2$ contain a "polymer moiety", which is characterized by one or more repeating units, which may be randomly, block wise or alternating distributed. In addition, the at least three polymer chains $S^0$, $S^1$, $S^2$ show an end group, which is typically a hydrogen atom or an alkyl group having from 1 to 6 carbon atoms, which may be branched or unbranched, e.g. a methyl group, especially for PEG based polymer chains resulting in so called mPEGs. The term "PEG-based" as understood herein is applied to a polymer of which the mass proportion of PEG is at least 10% by weight, preferably at least 25%, and more preferably at least 50% based on the total weight of the polymer chain.

It is pointed out that the polymer moieties within the at least three polymer chains $S^0$, $S^1$, $S^2$ may have further chain-like substituents, originating from the repeating units and resulting in chains having less than 4 kDa of molecular weight and which are not considered as polymer chains $S^0$, $S^1$, $S^2$, etc. Preferably, the at least three polymer chains $S^0$, $S^1$, $S^2$ carry substituents of less than 1000 Da molecular weight.

A relevant structural feature of $S^0$ is its critical distance. The critical distance defines the shortest distance between the attachment site of $S^0$ to $L^a$ and the first branching structure $BS^1$ measured as connected atoms. The length of the critical distance has an effect on the residual activity as discussed for compound 33 as described in WO-A 2009/133137, which is hereby incorporated by reference. The critical distance is preferably less than 50, more preferred less than 20, and most preferred less than 10.

The at least three polymer chains $S^0$, $S^1$ and $S^2$ typically each contain an interconnecting moiety. $G^a$ is present in at least one of the interconnecting moieties. For polymer chains other than $S^0$, the interconnecting moiety is the structural element connecting the polymer moiety of for instance $S^1$ with $BS^1$ and the polymer moiety of $S^2$ with $BS^2$. For $S^0$, the interconnecting moiety is the structural element connecting $L^a$ and $BS^1$.

Interconnecting moieties may consist of a $C_{1-50}$ alkyl chain, which is branched or unbranched and which is optionally interrupted or terminated by hetero atoms or functional groups selected from the group consisting of —O—; —S—; N(R); C(O); C(O)N(R); N(R)C(O); one or more carbocycles or heterocycles, wherein R is hydrogen or a $C_{1-20}$ alkyl chain, which is optionally interrupted or terminated by one or more of the abovementioned atoms or groups, which further have a hydrogen as terminal atom; and wherein a carbocycle is phenyl; naphthyl; indenyl; indanyl; tetralinyl; $C_{3-10}$ cycloalkyl; and wherein the heterocycle is a 4 to 7 membered heterocyclyl; or 9 to 11 membered heterobicyclyl.

"$C_{3-10}$ cycloalkyl" or "$C_{3-10}$ cycloalkyl ring" means a cyclic alkyl chain having 3 to 10 carbon atoms, which may have carbon-carbon double bonds being at least partially saturated, e.g. cyclopropyl, cyclobutyl, cyclopentyl, cyclohexyl, cyclohexenyl, cycloheptyl, cyclooctyl, cyclononyl, cyclodecyl. Each hydrogen of a cycloalkyl carbon may be replaced by a substituent. The term "$C_{3-10}$ cycloalkyl" or "$C_{3-10}$ cycloalkyl ring" also includes bridged bicycles like norbonene or norbonene.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes Spiro structures of two rings like 1,4-dioxa-8-azaspiro[4.5]decane or bridged heterocycles like 8-aza-bicyclo[3.2.1]octane.

The carbocycle, heterocycle and heterobicycle may be substituted by $C_{1-20}$ alkyl, optionally interrupted or terminated by hetero atoms or functional groups selected from the group consisting of —O—; —S—; N(R); C(O); C(O)N(R); N(R)C(O), wherein R is hydrogen or a $C_{1-10}$ alkyl chain, which is optionally interrupted or terminated by one or more of the abovementioned atoms or groups, which further have a hydrogen as terminal atom.

The polymer moiety of the at least three chains $S^0$, $S^1$, $S^2$ form the majority part of the chains, preferably at least 90% of the molecular weight of each chain, more preferred at least 95%, even more preferred at least 97.5% even more preferred at least 99%. Thus, the basis of the chains is represented by the polymer moiety.

Preferably, the at least three chains $S^0$, $S^1$, $S^2$ are independently based on a polymer selected from the group consisting of polyalkyloxy polymers, hyaluronic acid and derivatives thereof, polyvinyl alcohols, polyoxazolines, polyanhydrides, poly(ortho esters), polycarbonates, polyurethanes, polyacrylic acids, polyacrylamides, polyacrylates, polymethacrylates, polyorganophosphazenes, polysiloxanes, polyvinylpyrrolidone, polycyanoacrylates, and polyesters.

Preferably, the at least three chains $S^0$, $S^1$, $S^2$ are based on the same polymer. Preferably, the at least three chains $S^0$, $S^1$, $S^2$ are based on polyalkyoxy polymers. Even more preferred the at least three chains $S^0$, $S^1$, $S^2$ are polyethylene glycol based.

The same applies for further chains $S^3$, $S^4$, $S^5$, etc, accordingly.

The chain $S^0$ comprises a branching structure $BS^1$, so that $S^1$ is linked to $S^0$. For the linkage of $S^2$ the branching structure $BS^1$ may be used or a further branching structure $BS^2$ is present, which may be a part $S^0$ or $S^1$. Accordingly, further branching structures may be present, when further chains are present. For example in case a chain $S^3$ is present it may be linked to $BS^1$, $BS^2$ or a branching structure $BS^3$. The branching structure $BS^3$, if present, may be part of $S^0$, $S^1$, or $S^2$.

In general any chemical entity, which allows the branching of a chain, may be used. Preferably, the branching structures are independently selected from the group consisting of at least 3-fold substituted carbocycle, at least 3-fold substituted heterocycle, a tertiary carbon atom, a quaternary carbon atom, and a tertiary nitrogen atom, wherein the terms carbocycle and heterocycle are defined as indicated above.

In publications in the field of auto-cleavage inducing groups are sometimes called linkers to discriminate their structure from the carrier. Nevertheless it is often difficult to clearly separate these structural features. Therefore, within the meaning of the present invention the cleavage-inducing group $G^a$ is considered to be part of the carrier S, comprising at least $S^0$, $S^1$, $BS^1$, and optionally $BS^2$. Variation of the chemical nature of $G^a$ allows the engineering of the properties of the self-cleaving properties of a corresponding carrier-linked prodrug to a great extent.

As discussed above, a PEGylated-prodrug, wherein the drug is for example rhGH as described in patent application WO-A 2005/099768, and has a characteristic of release, which is therein described as the 1,6 cleavage system without the production of toxic aromatic compounds. In this document is broadly described numerous herein relevant suitable transient linker structures to get a relevant release profile of interest. Other transient linker structures are generically/broadly described in e.g. other Complex Biosystems GmbH applications such as WO-A 2005/034909, WO-A 2005/099768, WO-A 2006/003014 and WO-A 2006/136586.

More transient linker structures are broadly described in e.g. WO-A 99/30727 (Enzon Inc).

In order to solve the present problems for GH as discussed herein, the present inventors have selected suitable preferred transient linker structures to get the herein described relevant functional properties of the rhGH PEGylated prodrug. Based on the herein detailed description of preferred linker structures it is within the skilled person knowledge to make other suitable preferred transient linker structures that could give an rhGH PEGylated prodrug with the herein described relevant functional properties.

Especially, suitable transient linker structures, which are self hydrolysable (auto-cleavable) can be chosen for incorporation into $S^0$. The herein selected linker structures are described in detail below.

In order to introduce hydrolytic lability into functional groups L such as amides or carbamates, it is necessary to engineer structural chemical components into the carrier in order to function, for instance, as neighbouring groups in proximity to the functional group. Such autocleavage-inducing chemical structures that exert control over the cleavability of the prodrug amide bond are termed auto-cleavage inducing groups $G^a$. Autocleavage-inducing groups can have a strong effect on the rate of hydrolysis of a given functional group $L^a$.

Preferred $L^a$ are selected from the group consisting of C(O)—O—, and C(O)—, which form together with the primary amino group of hGH a carbamate or amide group.

Thus, a composition of the present invention is preferred, wherein $L^a$ is selected from the group consisting of C(O)—O—, and C(O)—, which form together with the primary amino group of hGH a carbamate or amide group resulting in formula (AA1) or (AA2)

hGH—NH—C(O)O—$S^0$ (AA1),

hGH—NH—C(O)—$S^0$ (AA2).

The following sections will list various structural components that may function as cleavage-inducing groups $G^a$.

The group $G^a$ represents an autocleavage inducing group. $G^a$ may be present as such or as a cascade autocleavage-inducing group, which is unmasked to become effective by means of an additional hydrolytical or enzymatic cleavage step. If $G^a$ is present as such, it governs the rate-limiting autohydrolysis of $L^a$.

Examples for $G^A$:

A. J. Garman et al. (A. J. Garman, S. B. Kalindjan, FEBS Lett. 1987, 223 (2), 361-365 1987) used PEG5000-maleic anhydride for the reversible modification of amino groups in tissue-type plasminogen activator and urokinase. Regeneration of functional enzyme from PEG-uPA conjugate upon incubation at pH 7.4 buffer by cleavage of the maleamic acid linkage followed first order kinetics with a half-life of 6.1 h.

Simple aromatic moieties may infer lability to a connected carbamate bond (WO-A 01/47562). For instance, substituted or unsubstituted fluorenylmethyl group were used to labilize carbamate linkages to various bioactive agents in a prodrug approach (Tsubery et al. J Biol Chem 279 (2004) 38118-24). Two PEG chains were attached to a fluorenyl moiety in WO-A 2007/075534.

Thus, $G^a$ is an aromatic ring or fluorenylmethyl directly attached to a carbamate functional group $L^a$.

Accordingly, a composition of the present invention is preferred, wherein $G^a$ is an aromatic ring or fluorenylmethyl directly attached to a carbamate functional group formed by $L^a$ and the primary amino group of hGH.

Alternatively, transformation of $G^a$ may induce a molecular rearrangement within such as a 1,4- or 1,6-elimination. The rearrangement renders $L^a$ more labile so that its cleavage is induced. The transformation of $G^a$ is the rate-limiting step in the cascade mechanism. Ideally, the cleavage rate of the temporary linkage is identical to the desired release rate for the drug molecule in a given therapeutic scenario. In such a cascade system based on 1,6-elimination, it is desirable that the cleavage of $L^a$ is substantially instantaneous after its lability has been induced by transformation of $G^a$. In addition it is desirable that the rate-limiting cleavage kinetics proceed in a therapeutically useful timeframe without the requirement for additional enzymatic contribution in order to avoid the drawbacks associated with predominantly enzymatic cleavage discussed above.

R. B. Greenwald, A. Pendri, C. D. Conover, H. Zhao, Y. H. Choe, A. Martinez, K. Shum, S. Guan, J. Med. Chem., 1999, 42, 3657-3667 & PCT Patent Application WO-A 99/30727 described a methodology for synthesizing poly (ethylene glycol) prodrugs of amino-containing small molecule compounds based on 1,4- or 1,6-benzyl elimination. In this approach the amino group of the drug molecule is linked via a carbamate group to a PEGylated benzyl moiety. The polyethylene glycol) was attached to the benzyl group by ester, carbonate, carbamate, or amide bonds. The release of PEG from the drug molecule occurs through a combination of autohydrolysis and enzymatic cleavage. The cleavage of the release-triggering masking group is followed in this approach by the classical and rapid 1,4- or 1,6-benzyl elimination. This linker system was also used for releasable poly(ethylene glycol) conjugates of proteins (S. Lee, R. B. Greenwald et al. Bioconj. Chem. 2001, 12 (2), 163-169). Lysozyme was used as model protein because it loses its activity when PEGylation takes place on the epsilon-amino group of lysine residues. Various amounts of PEG linker were conjugated to the protein. Regeneration of native protein from the PEG conjugates occurred in rat plasma or in non-physiological high pH buffer. See also F. M. H. DeGroot et al. (WO-A 2002/083180 and W0-A 2004/043493), and D. Shabat et al. (WO-A 2004/019993).

Thus, $L^a$ is a carbamate functional group, the cleavage of said group is induced by a hydroxyl or amino group of $G^a$ via 1,4- or 1,6 benzyl elimination of $S^0$, wherein $G^a$ contains ester, carbonate, carbamate, or amide bonds that undergo rate-limiting transformation. In effect, $G^a$ may be cleaved off by hydrolysis.

Accordingly, a composition of the present invention is preferred, wherein $L^a$ forms together with the amino group of hGH a carbamate functional group, the cleavage of said group is induced by a hydroxyl or amino group of $G^a$ via 1,4- or 1,6 benzyl elimination of $S^0$, wherein $G^a$ contains ester, carbonate, carbamate, or amide bonds that undergo rate-limiting transformation.

$G^a$ may contain a cascade cleavage system that is enabled by components of $G^a$ that are composed of a structural combination representing the aforementioned precursor. A precursor of $G^a$ may contain additional temporary linkages such as an amide, ester or a carbamate. The stability or susceptibility to hydrolysis of the precursor's temporary linkage (e.g. carbamate) may be governed by autohydrolytic properties or may require the activity of an enzyme.

Antezak et al. (Bioorg Med Chem 9 (2001) 2843-48) describe a reagent which forms the basis for a macromolecular cascade prodrug system for amine-containing drug molecules. In this approach an antibody serves as the carrier, a stable bond connects the antibody to an activating group, carrying a cleavable masking group. Upon removal of the ester-linked masking group, $L^a$ cleaves and releases the drug compound.

D. Shabat et al. (Chem. Eur. 3. 2004, 10, 2626-2634) describe a polymer prodrug system based on a mandelic acid activating group. In this system the masking group is linked to the activating group by a carbamate bond. The activating group is conjugated permanently to a polyacrylamide polymer via an amide bond. After activation of the masking group by a catalytic antibody, the masking group is cleaved by cyclization and the drug is released. The activating group is still connected to the polyacrylamide polymer after drug release.

M.-R. Lee et al. describe (Angew. Chem. 2004, 116, 1707-17 10) a similar prodrug system based on a mandelic acid activating group and an ester-linked masking group. Nevertheless in these linkers a 1,6-elimination step still generates a highly reactive aromatic intermediate. Even if the aromatic moiety remains permanently attached to the polymer carrier, side reactions with potentially toxic or immunogenic effects may be caused.

Greenwald et al. published in 2000 a poly(ethylene glycol) drug delivery system of amino-containing prodrugs based on trimethyl lock lactonization (R. B. Greenwald et al. J. Med. Chem. 2000, 43(3), 457-487; WO-A 02/089789). In this prodrug system substituted o-hydroxyphenyl-dimethylpropionic acid is coupled to amino groups of drug molecules by an amide bond. The hydroxy group is linked to PEG by an ester, carbonate, or carbamate group. The rate determining step in drug release is the enzymatic cleavage of these functional groups followed by fast amide cleavage by lactonization, liberating an aromatic lactone side product.

More recently, R. B. Greenwald et al. (Greenwald et al. J. Med. Chem. 2004, 47, 726-734) described a PEG prodrug system based on bis-(N-2-hydroxyethyl)glycin amide (bicin amide) linker. In this system two PEG molecules are linked to a bicin molecule coupled to an amino group of the drug molecule. The first two steps in prodrug activation is the enzymatic cleavage of both PEG molecules. Different linkages between PEG and bicin are described resulting in different prodrug activation kinetics. The main disadvantage of this system is the slow hydrolysis rate of bicin amide conjugated to the drug molecule ($t_{1/2}$=3 h in phosphate buffer) resulting in the release of a bicin-modified prodrug intermediate that may show different pharmacokinetic and pharmacodynamic properties than the parent drug molecule.

More specifically, preferred groups $L^a$ and $G^a$ with specific spacer moieties for $S^0$ are described below.

A preferred structure according to WO-A 2005/099768 is selected from the general formula (I) and (II):

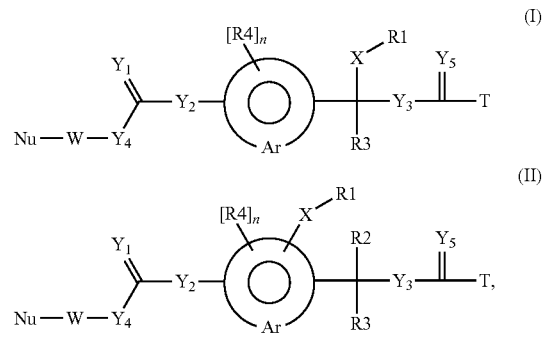

wherein in these formulae T represents hGH-NH; X represents a spacer moiety; $Y_1$ and $Y_2$ each independently represent O, S or NR6; $Y_3$ and $Y_5$ independently of each other represent O or S; $Y_4$ represents O, NR6 or —C(R7)(R8); R2 and R3 independently of each other represent a moiety selected from the group consisting of hydrogen, substituted or unsubstituted linear, branched or cyclical alkyl or heteroalkyl groups, aryls, substituted aryls, substituted or unsubstituted heteroaryls, cyano groups, nitro groups, halogens, carboxy groups, carboxyalkyl groups, alkylcarbonyl groups or carboxamidoalkyl groups; R4 represents a moiety selected from the group consisting of hydrogen, substituted or unsubstituted linear, branched or cyclical alkyls or heteroalkyls, aryls, substituted aryls, substituted or unsubstituted heteroaryl, substituted or unsubstituted linear, branched or cyclical alkoxys, substituted or unsubstituted linear, branched or cyclical heteroalkyloxys, aryloxys or heteroaryloxys, cyano groups and halogens; R7 and R8 are each independently selected from the group consisting of hydrogen, substituted or unsubstituted linear, branched or cyclical alkyls or heteroalkyls, aryls, substituted aryls, substituted or unsubstituted heteroaryls, carboxyalkyl groups, alkylcarbonyl groups, carboxamidoalkyl groups, cyano groups, and halogens; R6 represents a group selected from hydrogen, substituted or unsubstituted linear, branched or cyclical alkyls or heteroalkyls, aryls, substituted aryls and substituted or unsubstituted heteroaryls; R1 represents the rest of $S^0$; W represents a group selected from substituted or unsubstituted linear, branched or cyclical alkyls, aryls, substituted aryls, substituted or unsubstituted linear, branched or cyclical heteroalkyls, substituted or unsubstituted heteroaryls; Nu represents a nucleophile; n represents zero or a positive imager; and Ar represents a multi-substituted aromatic hydrocarbon or multi-substituted aromatic heterocycle.

Within the meaning of the present invention, the group $L^a$ is represented by $Y_3$—C($Y_5$)NH— (together with the amino group of hGH), $G^a$ is represented by Nu-W—$Y_4$—C($Y_1$)$Y_2$ and Ar(R4)$_n$—C(R3)XR$_1$ represents $S^0$, which further includes at least $S^1$, $S^2$, $BS^1$ and optionally $BS^2$.

In an alternative embodiment $S^1$ is attached via Ar or represents R3. Then the carbon atom adjacent to $Y_3$ substituted with XR1 represents the branching structure $BS^1$, $S^1$ is terminated with Ar comprising $G^a$, it is evident that in this embodiment terms $S^0$ and $S^1$ are interchangeable.

Preferably, in formula (AA) or (AA1) $S^0$ is of formula (AAA1)

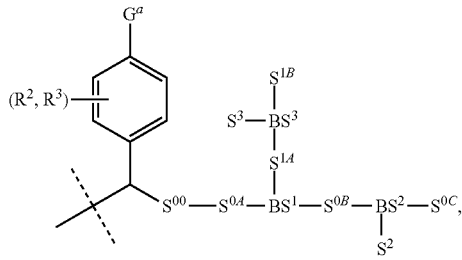

(AAA1)

wherein in formula (AAA1)
$G^a$ has the meaning as indicated above;
$S^{00}$ is $CH_2$; or $C(O)$;
$S^{0A}$ is an alkylene chain having from 1 to 20 carbon atoms, which is optionally interrupted or terminated by one or more groups, cycles or heteroatoms selected from the group consisting of optionally substituted heterocycle; O; S; C(O); and NH;
$BS^1$, $BS^2$, $BS^3$ are independently selected from the group consisting of N; and CH.
$S^{0B}$, $S^{1A}$ are independently an alkylene chain having from 1 to 200 carbon atoms, which is optionally interrupted or terminated by one or more groups, cycles or heteroatoms selected from the group consisting of optionally substituted heterocycle; O; S; C(O); and NH;
$S^{0C}$, $S^{1B}$, are $(C(O))_{n2}(CH_2)_{n1}(OCH_2CH_2)_nOCH_3$, wherein each n is independently an integer from 100 to 500, each n1 is independently 0, 1, 2, 3, 4, 5, 6, 7, or 8, and n2 is 0 or 1.
$S^2$, $S^3$ are independently hydrogen; or $(C(O))_{n2}(CH_2)_{n1}(OCH_2CH_2)_nOCH_3$, wherein each n is independently an integer from 100 to 500, each n1 is independently 0, 1, 2, 3, 4, 5, 6, 7, or 8, and n2 is 0 or 1, provided that at least one of $S^2$, $S^3$ is other than hydrogen;
$R^2$, $R^3$ are defined as for formula (A) below.

The term heterocycle means a heterocycle as defined above. Optional substituents are, e.g. oxo(=O), where the ring is at least partially saturated, a branched or unbranched alkyl chain having from one to 6 carbon atoms, or halogen. A preferred substituted heterocycle is succinimide.

Preferably, $G^a$ in formula (AAA1) is OC(O)—R and R is the partial structure of formula (I) as shown below, wherein R1, R4, R5 and n are defined as given below.

Another preferred embodiment is described in WO06136586A2. Accordingly, the following structures are preferred:

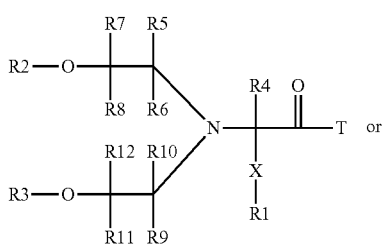

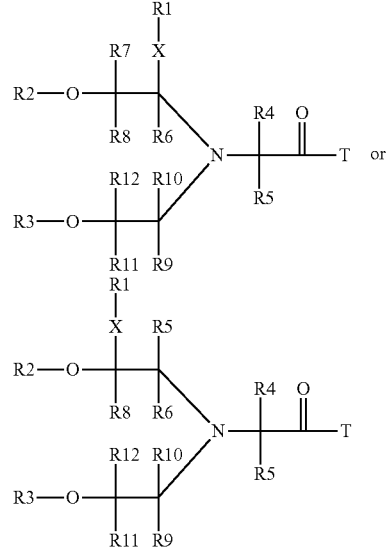

wherein in these three structures T is NH-hGH;
X is a spacer moiety such as R13-Y1;
Y1 is O, S, NR6, succinimide, maleimide, unsaturated carbon-carbon bonds or any heteroatom containing a free electron pair or is absent;
R13 is selected from substituted or non-substituted linear, branched or cyclical alkyl or heteroalkyl, aryls, substituted aryls, substituted or non-substituted heteroaryls;
R2 and R3 are selected independently from hydrogen, acyl groups, or protecting groups for hydroxyl groups;
R4 to R12 are selected independently from hydrogen, X—R1, substituted or non-substituted linear, branched or cyclical alkyl or heteroalkyl, aryls, substituted aryls, substituted or non-substituted heteroaryls, cyano, nitro, halogen, carboxy, carboxamide;
R1 is the rest of $S^0$, comprising at least $S^1$, $S^2$, $BS^1$, and optionally $BS^2$.

In this embodiment $L^a$ is an amide group, and $G^a$ encompasses the N-branched structure carrying $OR_2/OR_3$.

In yet another preferred embodiment, a preferred structure is given by a prodrug conjugate D-L, wherein
-D is NH-hGH; and
-L is a non-biologically active linker moiety $-L^1$ represented by formula (I),

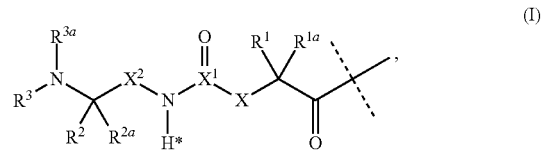

(I)

wherein in formula (I) the dashed line indicates the attachment to the amino group of hGH by forming an amide bond;
X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;
$X^1$ is C; or S(O);
$X^2$ is $C(R^7, R^{7a})$; or $C(R^7, R^{7a})$—$C(R^8, R^{8a})$;
$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or Optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

Optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, one or more of the pairs $R^1/R^4$, $R^1/R^5$, $R^1/R^6$, $R^4/R^5$, $R^7/R^8$, $R^2/R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $L^1$ is substituted with one group $L^2$-Z and optionally further substituted, provided that the hydrogen marked with the asterisk in formula (I) is not replaced by a substituent; wherein $L^2$ is a single chemical bond or a spacer; and Z is the rest of $S^0$, comprising at least $S^1$, $S^2$, $BS^1$, and optionally $BS^2$.

In this embodiment $L^a$ is represented by an amide group and $G^a$ is represented by $N(H^*)X^1(O)$ and the chain connecting to N including substituents of N.

Prodrug conjugates of this type are described in European Patent application No 08150973.9

Accordingly, a composition of the present invention is preferred, wherein $L^a$-$S^0$ is represented by formula (AAA2),

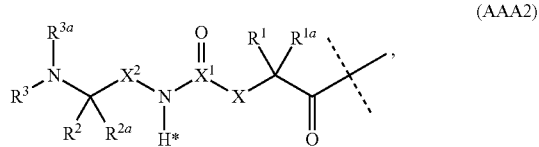

(AAA2)

wherein in formula (AAA2) the dashed line indicates the attachment to the primary amino group of hGH so that $L^a$ and the amino group form an amide bond;

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or Optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

Optionally, one or more of the pairs $R1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, one or more of the pairs $R^1/R^4$, $R^1/R^5$, $R^1/R^6$, $R^4/R^5$, $R^7/R^8$, $R^2$, $R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $S^0$ is substituted with one group $L^2$-Z and optionally further substituted, provided that the hydrogen marked with the asterisk in formula (AAA2) is not replaced by a substituent; wherein $L^2$ is a single chemical bond or a spacer; and Z is of formula (AAA2a)

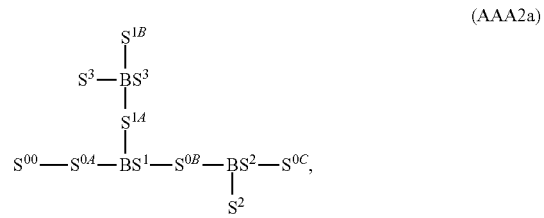

(AAA2a)

wherein $S^{00}$, $S^{OA}$, $S^{OB}$, $S^{OC}$, $S^{1A}$, $S^{1B}$, $S^2$, $S^3$, $BS^1$, $BS^2$, and $BS^1$ have the meaning as indicated for formula (AAA1) above.

"Alkyl" means a straight-chain or branched carbon chain. Each hydrogen of an alkyl carbon may be replaced by a substituent.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent. The term "$C_{1-8}$ alkyl" is defined accordingly.

Accordingly, "$C_{1-18}$ alkyl" means an alkyl chain having 1 to 18 carbon atoms and "$C_{8-18}$ alkyl" means an alkyl chain having 8 to 18 carbon atoms. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=CH, or e.g. —CH=CH—, when two moieties of a molecule are linked by the alkenyl group. Each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms, e.g. if present at the end of a molecule: —$CH_2$≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Each hydrogen of a $C_{2-50}$ alkynyl carbon may be replaced by a substituent as further specified. Accordingly, the term "alkynyl" relates to a carbon chain with at least one carbon carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent. The term "$C_{3-7}$ cycloalkyl" or "$C_{3-7}$ cycloalkyl ring" also includes bridged bicycles like norbonane or norbonene. Accordingly, "$C_{3-5}$ cycloalkyl" means a cycloalkyl having 3 to 5 carbon atoms.

Accordingly, "$C_{3-10}$ cycloalkyl" means a cyclic alkyl having 3 to 10 carbon atoms, e.g. $C_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

Preferably, $L^a$-$S^0$ is selected from the group consisting of

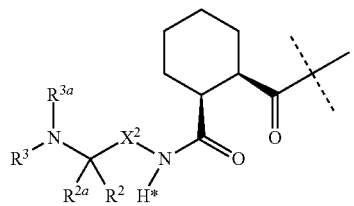

-continued

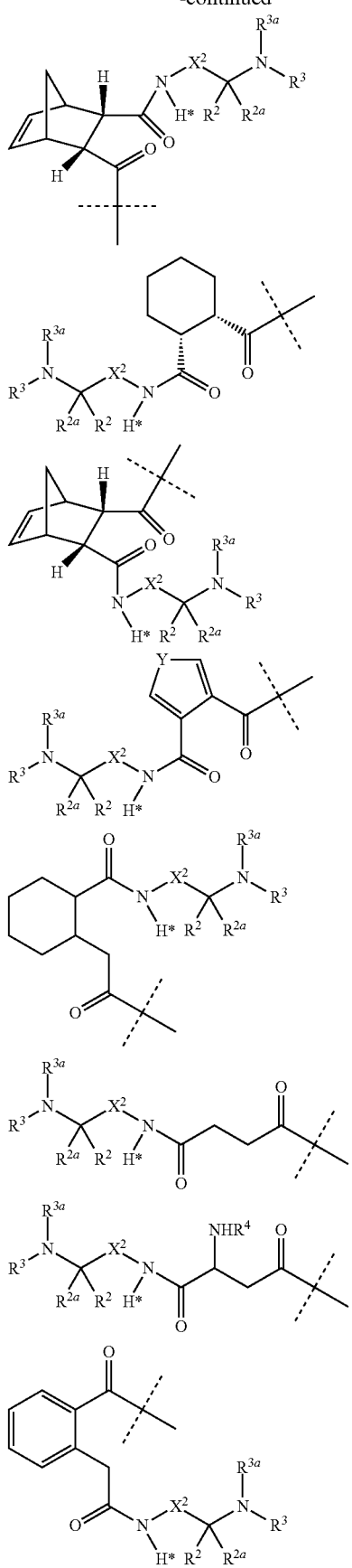

25
-continued
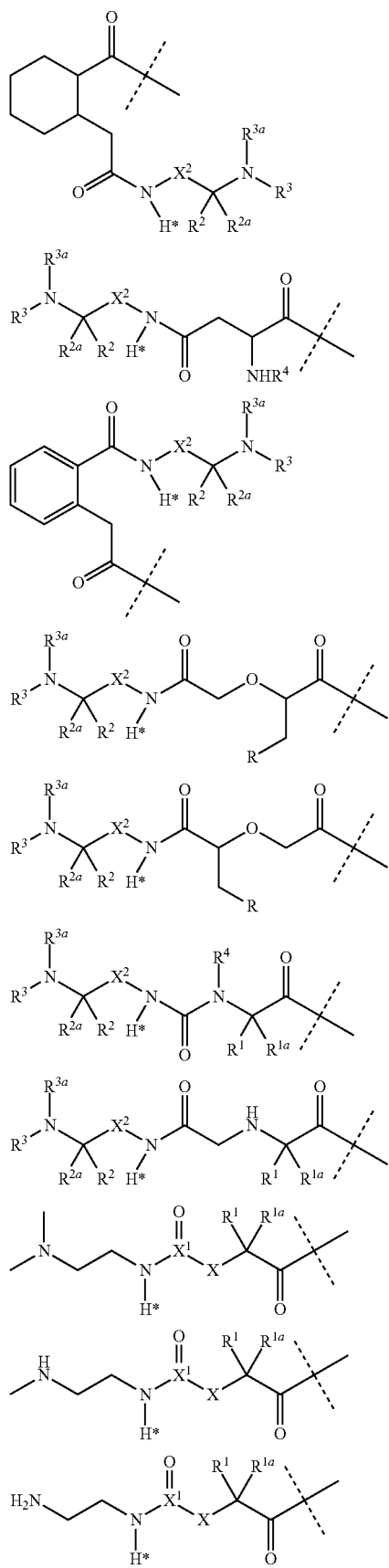
26
-continued
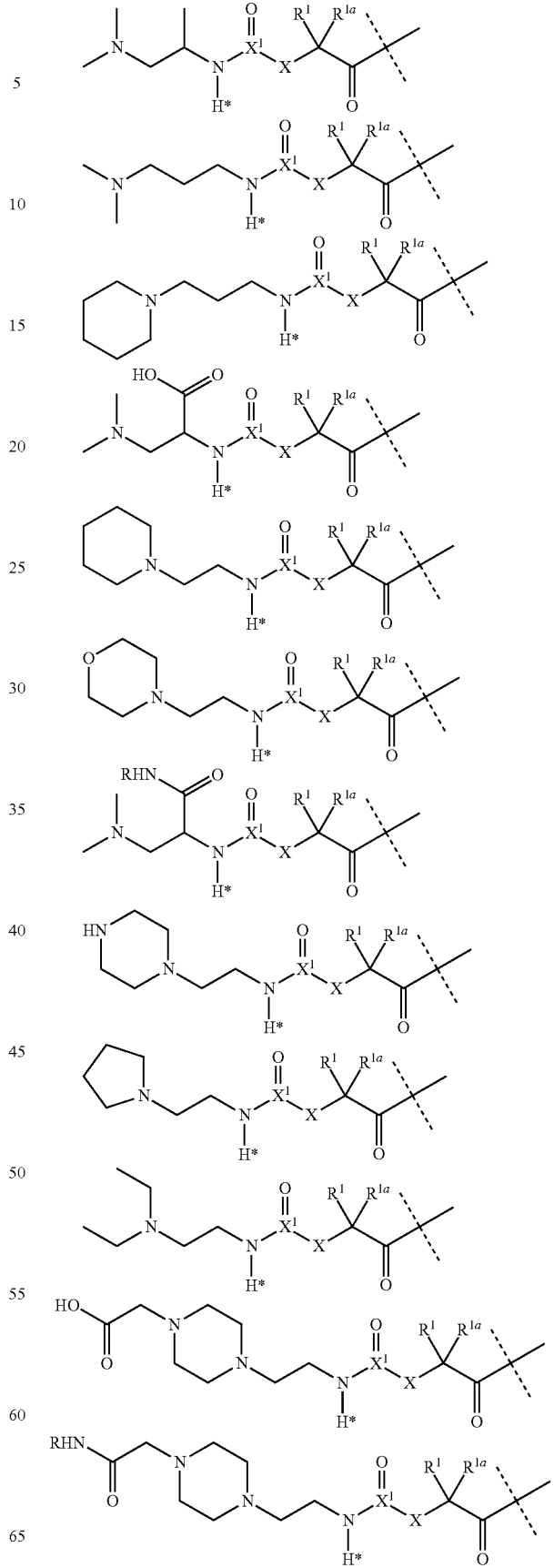

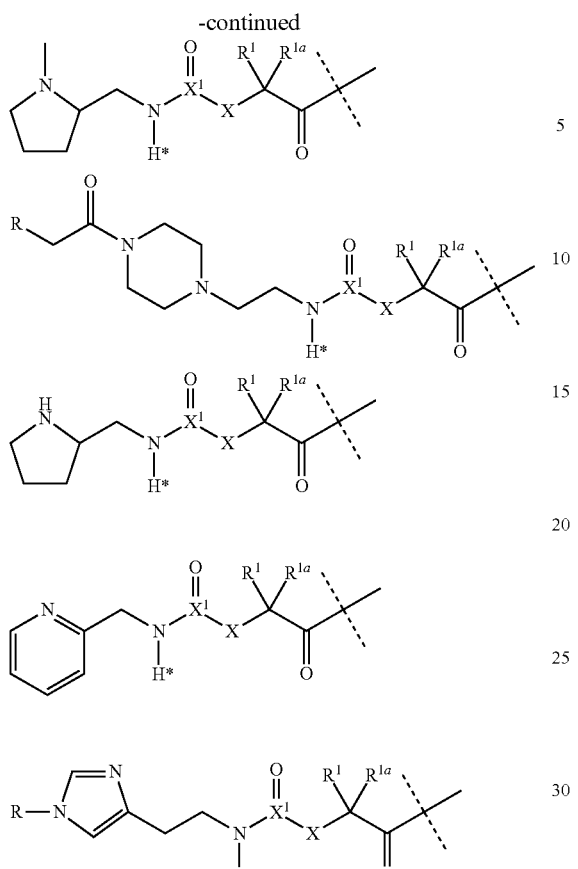
wherein R is H; or $C_{1-4}$ alkyl; Y is NH; O; or S; and $R^1$, $R^{1a}$, $R^2$, $R^{2a}$, $R^3$, $R^{3a}$, $R^4$, X, $X^1$, $X^2$ have the meaning as indicated above.
Even more preferred, $L^a$-$S^0$ is selected from the group consisting of
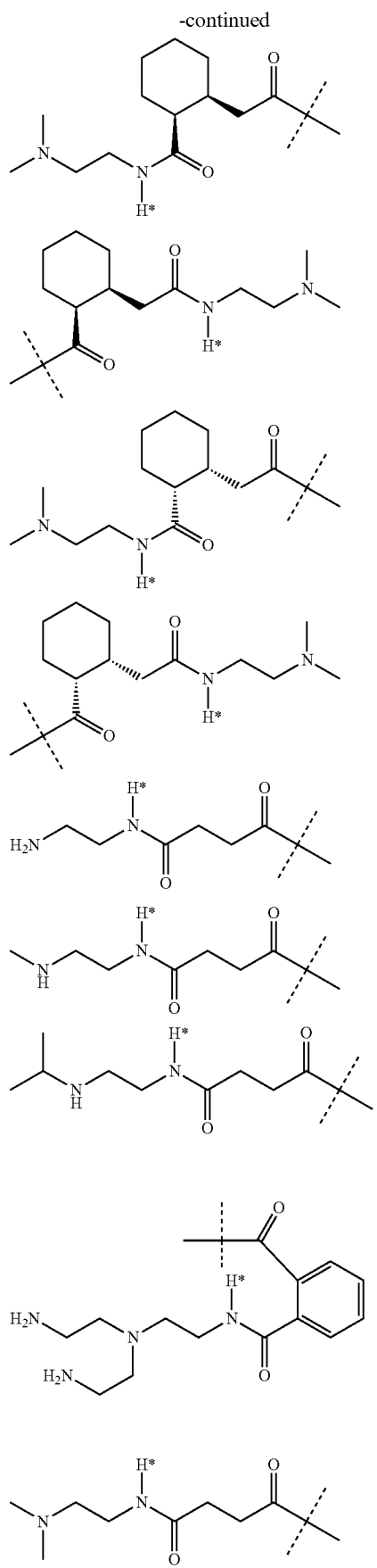

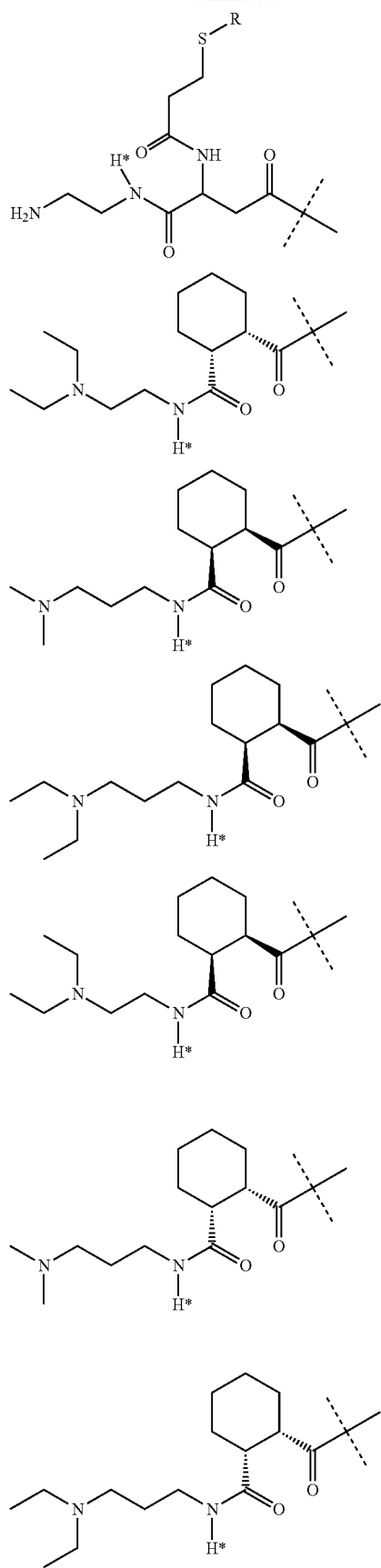
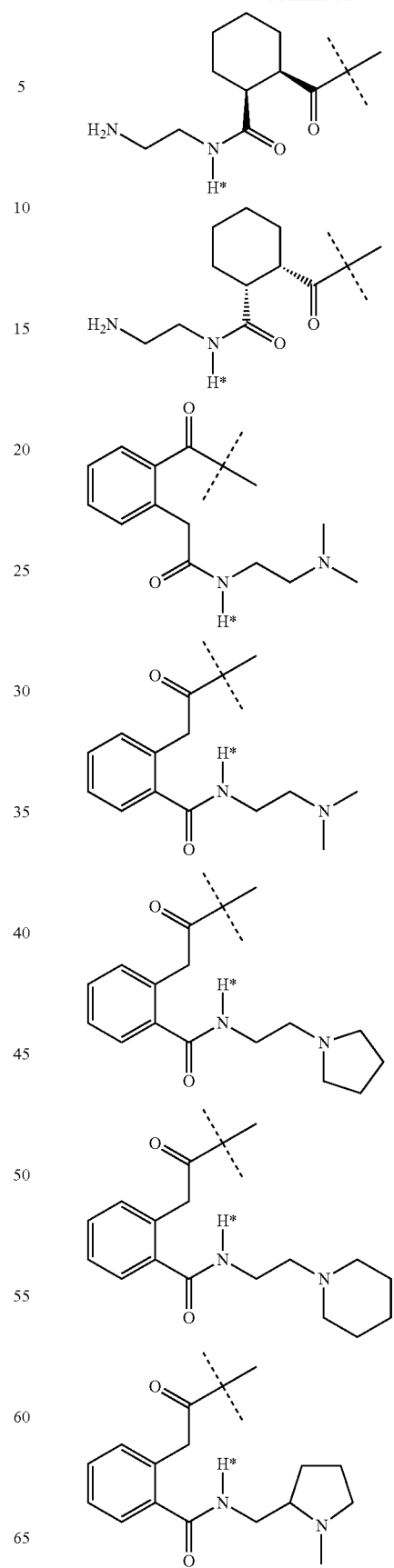

31
-continued
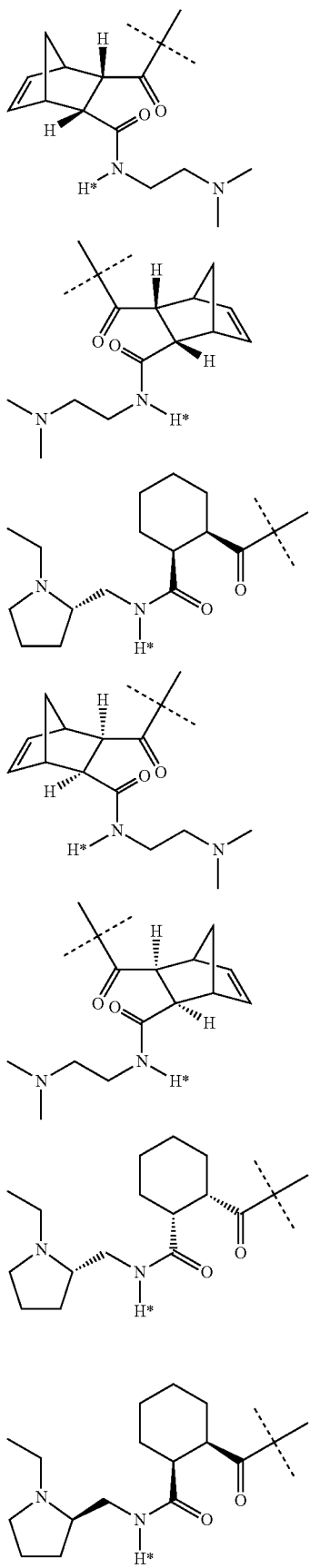
32
-continued
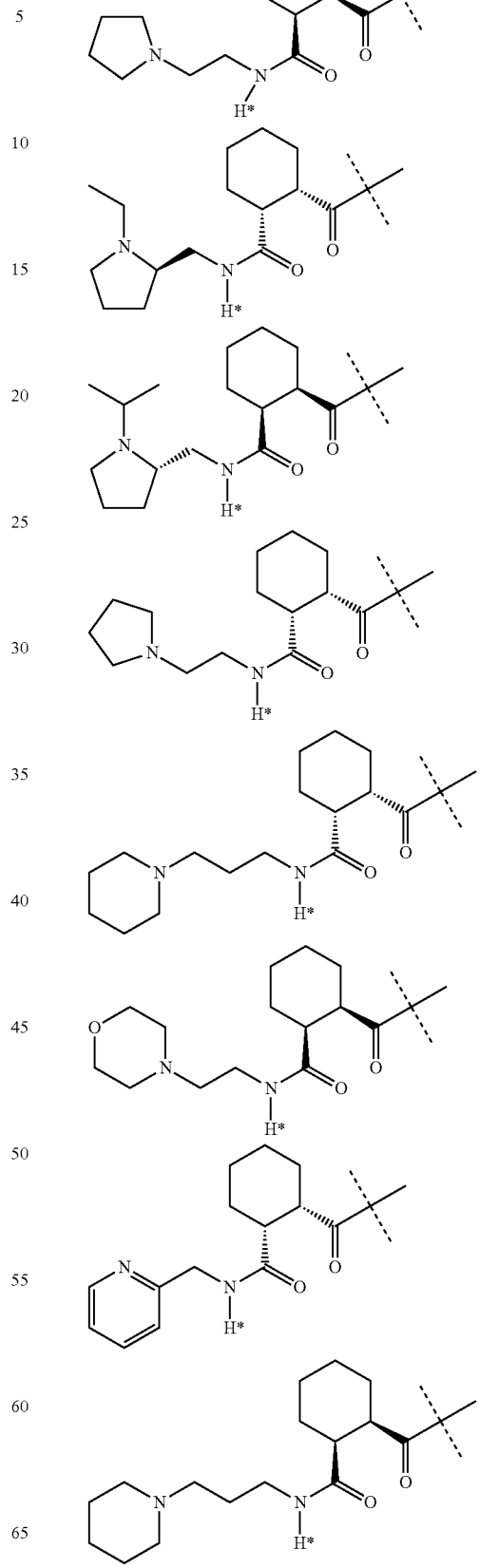

33
-continued
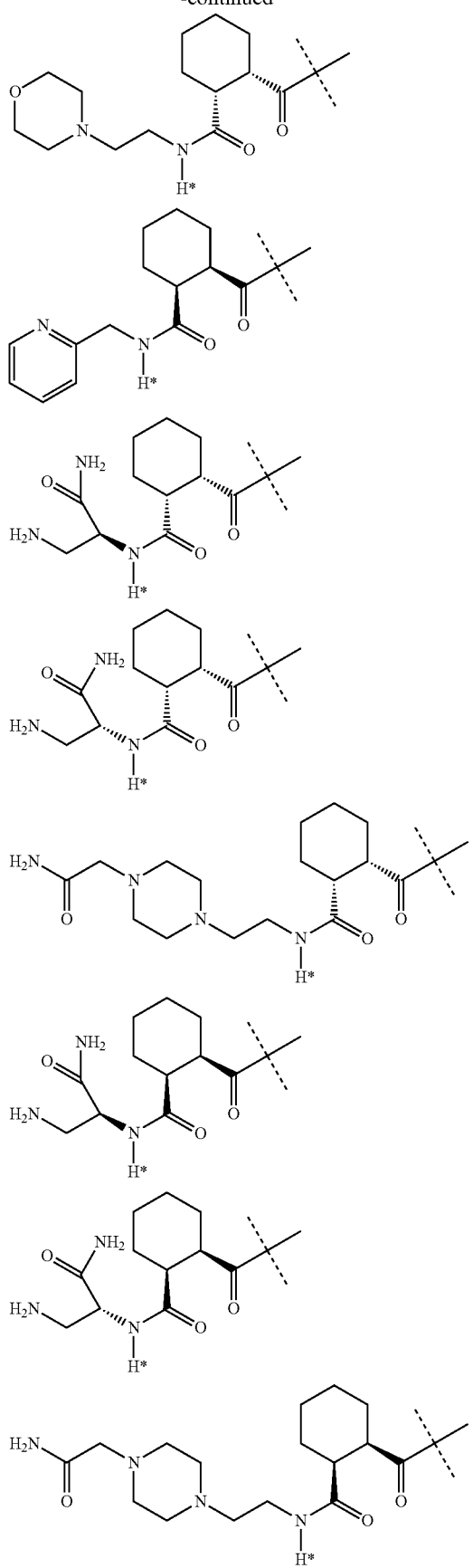
34
-continued
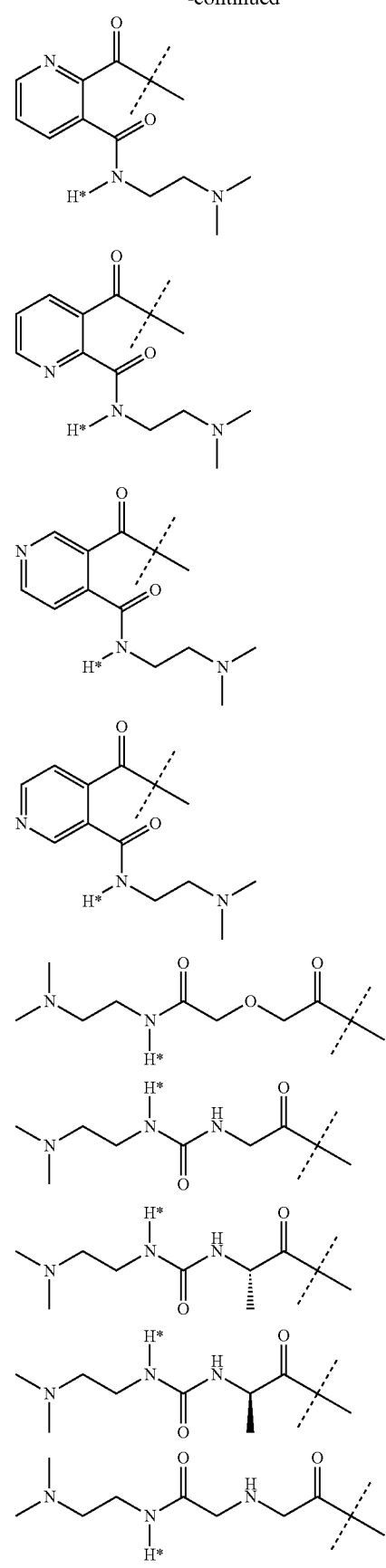

35
-continued
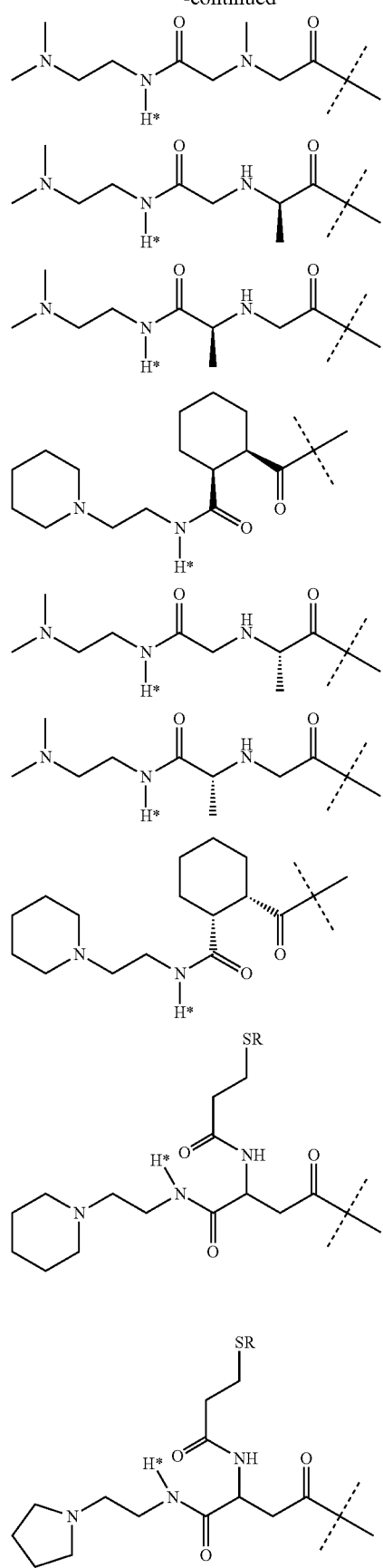
36
-continued
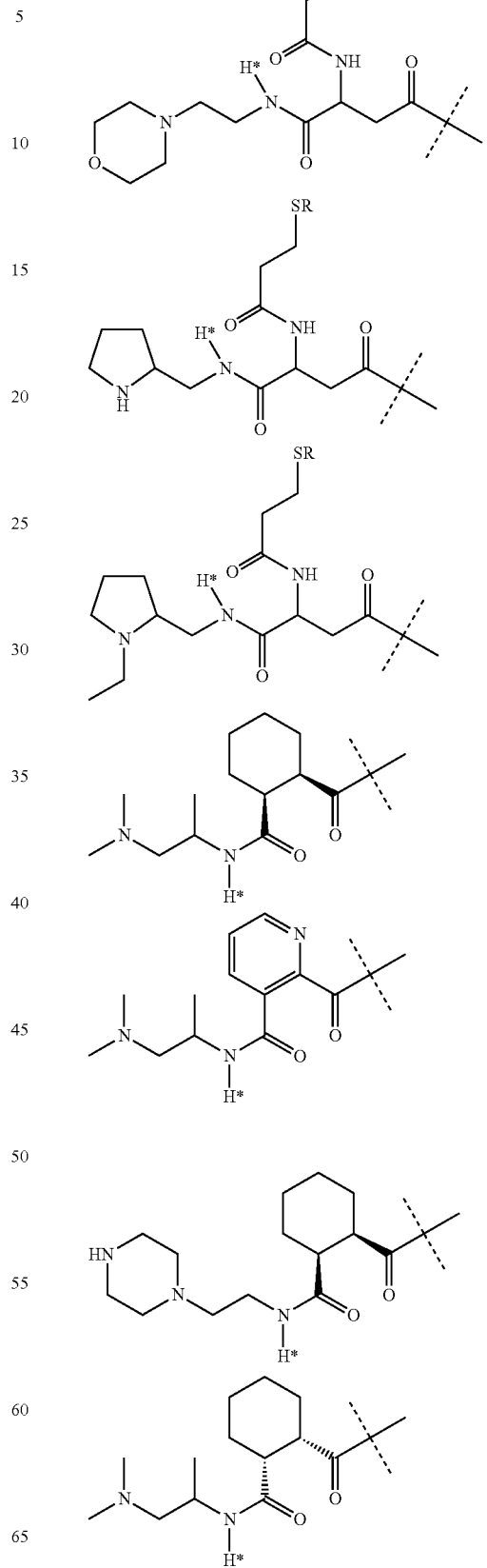

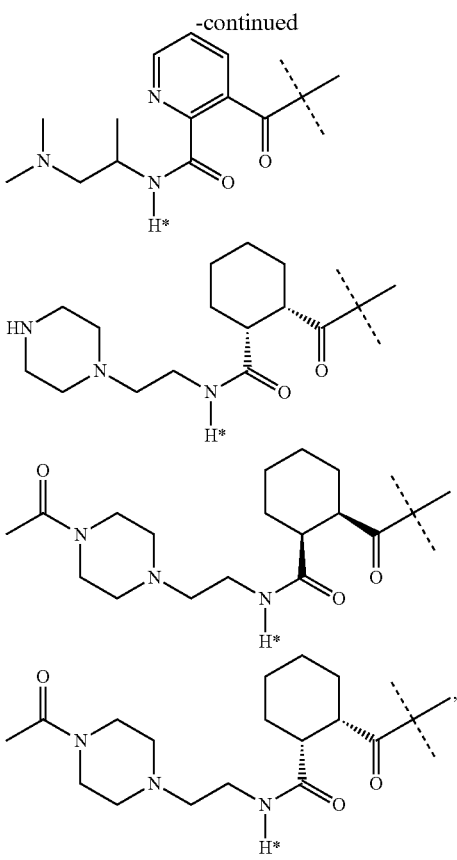

wherein R has the meaning as indicated above.

At least one (up to four) hydrogen is replaced by a group $L^2$-Z. In case more than one group $L^2$-Z is present each $L^2$ and each Z can be selected independently. Preferably, only one group $L^2$-Z is present.

In general, $S^0$ can be substituted with $L^2$-Z at any position apart from the replacement of the hydrogen marked with an asterisk in the formulae above. Preferably, one to four of the hydrogen given by R, $R^1$ to $R^8$ directly or as hydrogen of the $C_{1-4}$ alkyl or further groups and rings given by the definition of R and $R^1$ to $R^8$ are replaced by $L^2$-Z.

Furthermore, $S^0$ may be optionally further substituted. In general, any substituent may be used as far as the cleavage principle is not affected.

Preferably, one or more further optional substituents are independently selected from the group consisting of halogen; CN; $COOR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $SR^9$; $N(R^9R^{9a})$; $NO_2$; $OC(O)R^9$; $N(R^9)C(O)R^{9a}$; $N(R^9)S(O)_2R^{9a}$; $N(R^9)S(O)R^{9a}$; $N(R^9)C(O)OR^{9a}$; $N(R^9)C(O)N(R^{9a}R^{9b})$; $OC(O)N(R^9R^{9a})$; T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

$R^9$, $R^{9a}$, $R^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

T is selected from the group consisting of phenyl; naphthyl; indenyl; indenyl; tetralinyl; $C_{3-10}$ cycloalkyl; 4 to 7 membered heterocyclyl; or 9 to 11 membered heterobicyclyl, wherein T is optionally substituted with one or more $R^{10}$, which are the same or different;

$R^{10}$ is halogen; CN; oxo(=O); $COOR^{12}$; $OR^{12}$; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $SR^{12}$; $N(R^{12}R^{12a})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)OR^{12a}$; $N(R^{12})C(O)N(R^{12a}R^{12b})$; $OC(O)N(R^{12}R^{12a})$; or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or at the end of the carbon chain between the carbon and hydrogen.

$L^2$ is a single chemical bond or a spacer. In case $L^2$ is a spacer, it is preferably defined as the one or more optional substituents defined above, provided that $L^2$ is substituted with Z.

Accordingly, when $L^2$ is other than a single chemical bond, $L^2$-Z is $COOR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $SR^9$; $N(R^9R^{9a})$; $OC(O)R^9$; $N(R^9)C(O)R^{9a}$; $N(R^9)S(O)_2R^{9a}$; $N(R^9)S(O)R^{9a}$; $N(R^9)C(O)OR^{9a}$; $N(R^9)C(O)N(R^{9a}R^{9b})$; $OC(O)N(R^9R^{9a})$; T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of -T-, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

$R^9$, $R^{9a}$, $R^{9b}$ are independently selected from the group consisting of H; Z; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; S(O)N($R^{11}$)S(O)$_2$—; —S(O)—; —N($R^{11}$)S(O)$_2$N($R^{11a}$)—; —S—; —N($R^{11}$)—; —OC(O)$R^{11}$; —N($R^{11}$)C(O)—; N($R^{11}$)S(O)$_2$—; —N($R^{11}$)S(O)—; —N($R^{11}$)C(O)O—; —N($R^{11}$)C(O)N($R^{11a}$)—; and —OC(O)N($R^{11}R^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein t is optionally substituted with one or more $R^{10}$, which are the same or different;

$R^{10}$ is Z; halogen; CN; oxo(=O); $COOR^{12}$; $OR^{12}$; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12b})$; $SR^{12}$; $N(R^{12}R^{12a})$; $NO_2$; $OC(O)R^{12}$; $N(R^{12})C(O)R^{12a}$; $N(R^{12})S(O)_2R^{12a}$; $N(R^{12})S(O)R^{12a}$; $N(R^{12})C(O)OR^{12a}$; $N(R^{12})C(O)N(R^{12a}R^{12b})$; $OC(O)N(R^{12}R^{12a})$; or $C_{1-6}$ alkyl, wherein $C_{1-6}$ alkyl is optionally substituted with one or more halogen, which are the same or different;

$R^{11}$, $R^{11a}$, $R^{12}$, $R^{12a}$, $R^{12b}$ are independently selected from the group consisting of H; Z; or $C_{1-6}$ alkyl, wherein $C_{1-6}$ alkyl is optionally substituted with one or more halogen, which are the same or different;

provided that one of $R^9$, $R^{9a}$, $R^{9b}$, $R^{10}$, $R^{11}$, $R^{11a}$, $R^{12}$, $R^{12a}$, $R^{12b}$ is Z.

Even more preferred general aromatic structures are listed below.

Preferably, the hGH polymer prodrug has the structure given in formula (A).

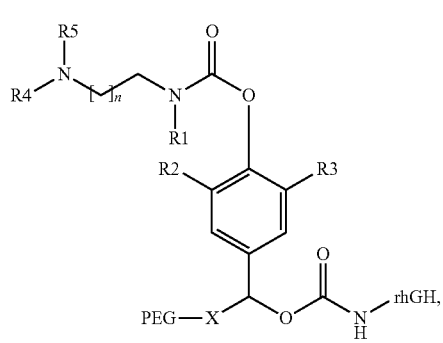
(A)

wherein in formula (A)
NH-rhGH represents the rhGH residue attached to the transient linker by forming a carbamate bond;
R1, R2, R3, R4, and R5 are selected independently from hydrogen, methyl, ethyl, propyl, isopropyl, butyl, isobutyl, tertiary butyl,
PEG represents a PEGylation residue attached to the transient linker, and n=1 or 2, and
X is selected from C1 to C8 alkyl or $C_1$ to $C_{12}$ heteroalkyl.

Preferably, the moiety

PEG-X— of formula (A) has the following structure

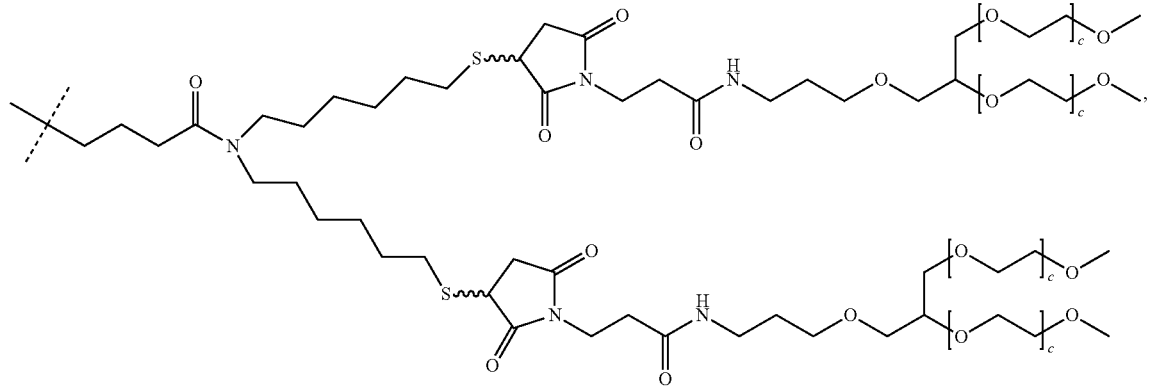

wherein each c is independently an integer from 250 to 750, preferably an integer from 300 to 400 and more preferably 500.

The term "C1 to C12 heteroalkyl" means an alkyl chain having 1 to 12 carbon atoms which are optionally interrupted by heteroatoms, functional groups, carbocycles or heterocycles as defined above. The term "C1 to C8 alkyl" means $C_{1-8}$ alkyl as defined above.

In a preferred embodiment, in formula (A) $L^a$ is represented by the carbamate group attached to rhGH, $G^a$ is represented by the aromatic oxygen group, the carbonyl attached to it, and the substituent attached to the carbonyl as shown in formula I below.

More preferred structures are given by general formula I, which are part of the structure (A) within the general aromatic linker structure above:

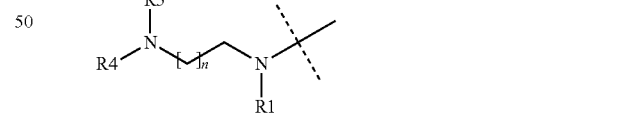
Formula I and where preferred examples of formula I comprise:

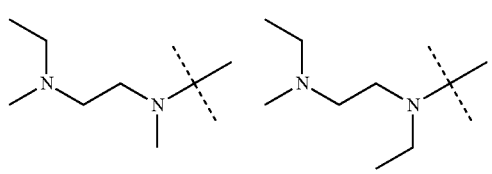

-continued
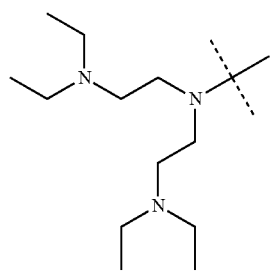
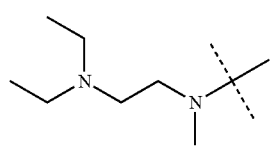
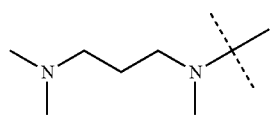
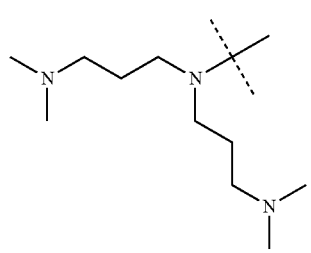
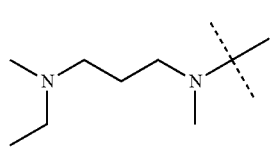
More preferred aromatic structures of formula II, which are part of the structure (A) within the general aromatic linker structure above:
Formula II
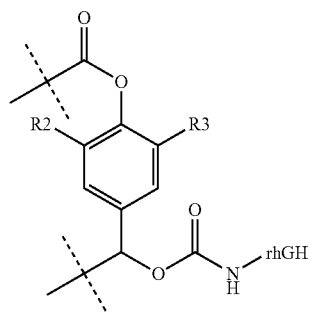
and where preferred examples of formula II comprise:
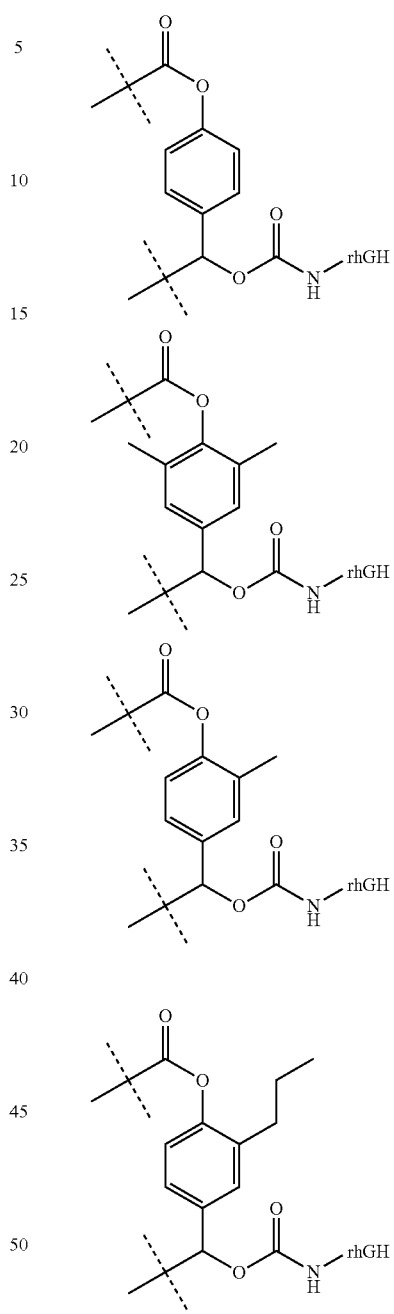
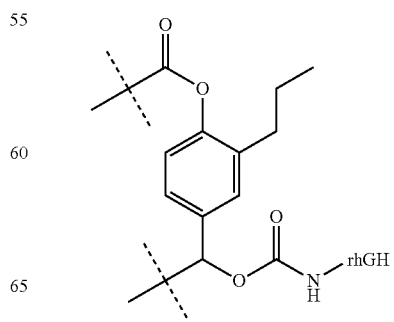

-continued

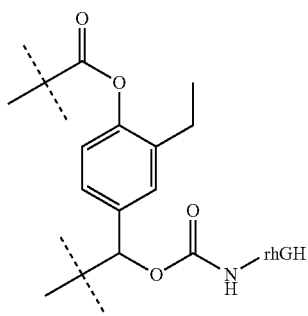

More preferred structures of formula III, which are part of the structure (A) within the general aromatic linker structure above, wherein PEG-X is Formula III

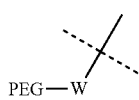

and PEG-W includes the following substituent groups:

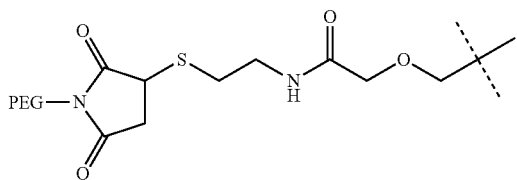

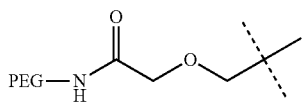

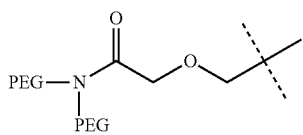

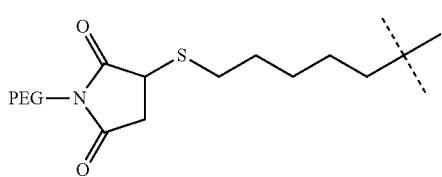

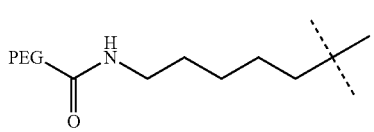

Further examples of preferred hGH polymer prodrug conjugates are shown below:

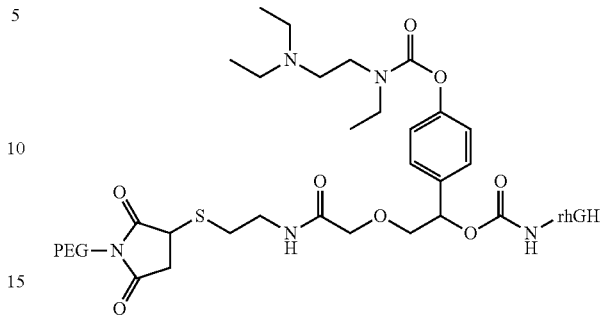

10

15

20

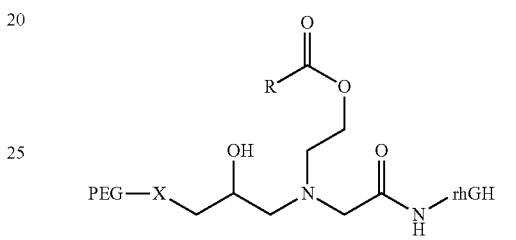

25

30

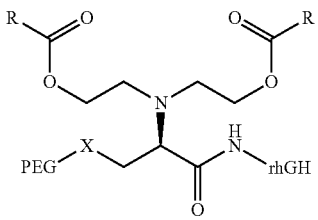

35

40

45

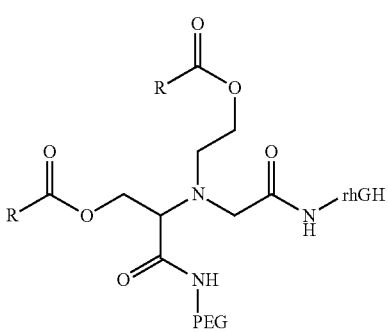

R is selected from hydrogen, methyl, ethyl, propyl and butyl,
X is selected from C1 to C8 alkyl or $C_1$ to $C_{12}$ heteroalkyl.

Also in the preferred and more preferred embodiments PEG means preferably the rest of $S^0$, comprising at least $S^1$, $S^2$, $BS^1$ and optionally $BS^2$.

In a preferred embodiment prodrugs comprised in the compositions of the present invention are selected from the group consisting of

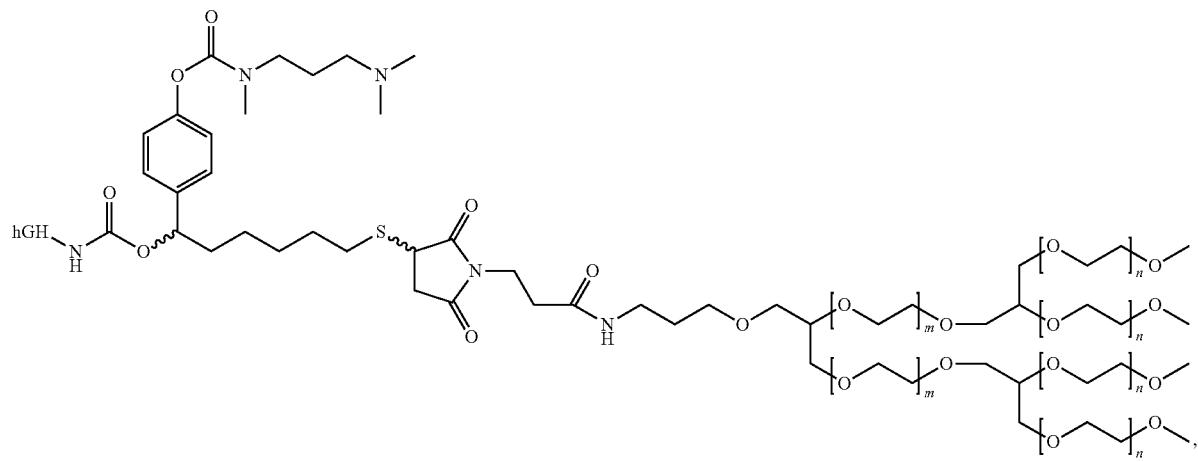
wherein m is an integer from 200 to 250 and n is an integer from 100 to 125;
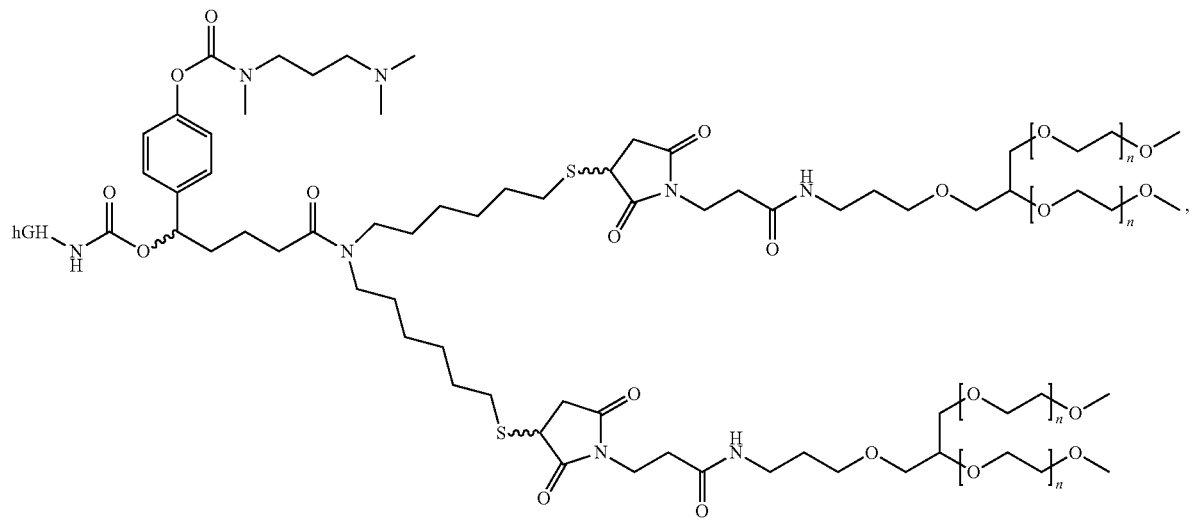
wherein n is an integer from 400 to 500;

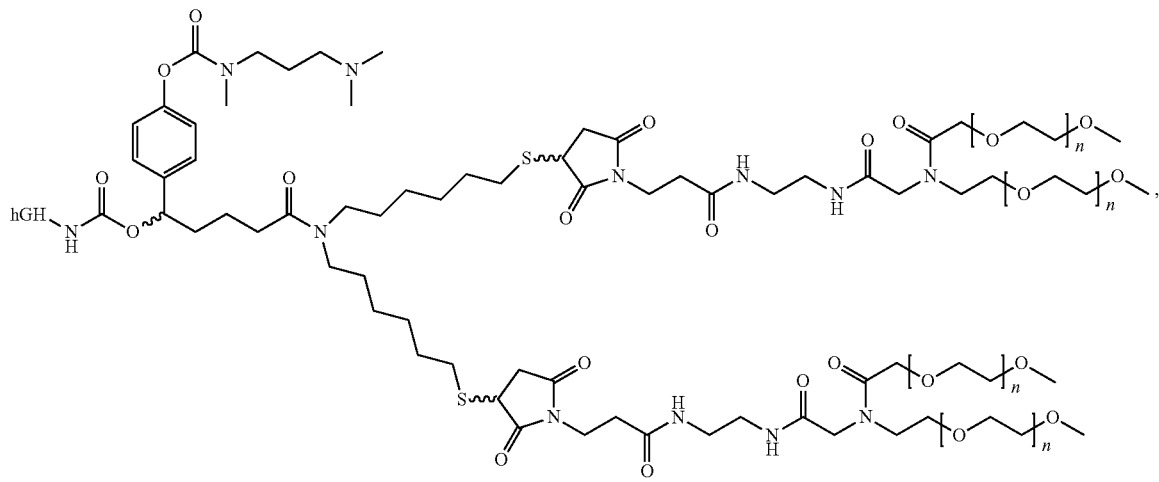

wherein n is an integer from 400 to 500; and

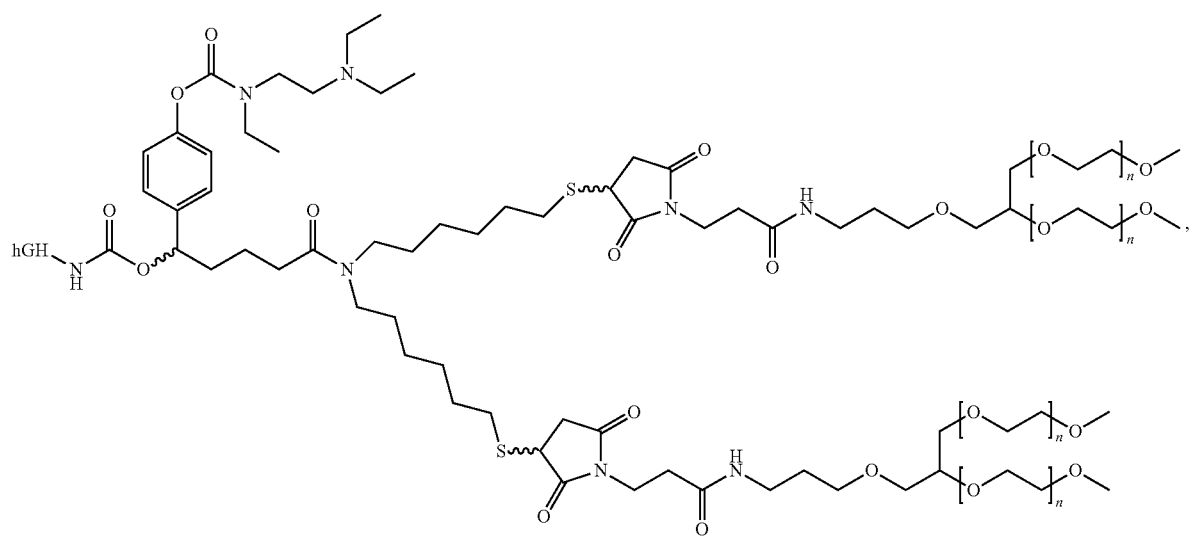

wherein n is an integer from 400 to 500.

Preferably, PEGylation of the hGH moiety occurs at one or more of the lysines selected from the group consisting of Lys158, Lys145, Lys38, Lys140 and Lys70. More preferably, PEGylation of the hGH moiety occurs mainly at positions Lys158, Lys145, Lys38 and Lys140, even more preferably mainly at positions Lys158, Lys145 and Lys38.

Preferably, at least 30% of all growth hormone moieties of the composition of the present invention are PEGylated at position Lys158.

hGH polymer prodrugs comprised in the dry compositions of the present invention can be prepared by methods known in the art. However, especially for compounds of formula (AA1) it is preferred to build up the prodrug molecule in a convergent synthesis by providing a first precursor molecule comprising one or more thiol groups and an activated carbonate group and a second precursor molecule comprising a maleimide group to react in an addition reaction resulting in the formation of a thio succinimide group and to react that combined precursor molecule with hGH to yield a compound of formula (AA1).

Accordingly, a method for the preparation of a compound of formula hGH-NH—C(O)O—S⁰ (AA1), wherein S⁰ has the meaning as indicated above and comprises at least one group

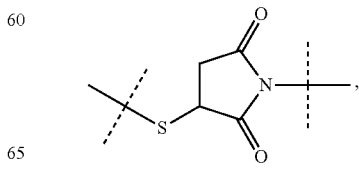

comprises the following steps:
(a) reacting a compound of formula ROC(O)O—S⁰′—SH (AA1') with a compound of formula

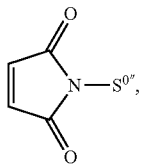

(AA2')

wherein R is a suitable rest for an activated carbonate group and wherein S⁰′ and S⁰′′′ are selected to yield S⁰ comprising the at least one group

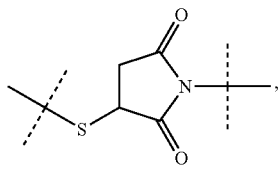

resulting in a compound of formula ROC(O)O—S⁰, and
(b) reacting the compound of formula ROC(O)O—S⁰ with hGH-NH₂, wherein hGH-NH₂ represents hGH with one of its primary amino groups to yield a compound of formula (AA1).

Suitable R groups for the carbonate functional groups include substituted alkyl or carbocyclic or heterocyclic, like aryl or cycloalkyl, groups like the pentafluorophenyl or NHS group.

The stable composition comprised of rhGH polymer prodrug as described above is a dry composition with a shelf-life of preferably at least 6 months, more preferably at least 1 year, more preferably at least 2 years, when stored at temperatures ranging from −80° C. up to 25° C., preferably ranging from 2 to 25° C. The preferred method of drying the rhGH polymer prodrug composition is lyophilization.

Thus a further aspect of the present invention is a composition which is dried by lyophilisation. Another aspect is a composition of the present invention which is stable for at least 1 year when stored at temperatures ranging from −80° C. up to 25° C., preferably ranging from 2-25° C. More preferably the temperature is from 2° C. to 8° C. Another preferred temperature range is from 15° C. to 25° C.

The dry composition of rhGH polymer prodrug according to the present invention comprises one or more lyoprotectants. Exemplary lyoprotectants include sugars, such as sucrose or trehalose; amino acids such as monosodium glutamate or histidine or arginine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ehthylene glycol; propylene glycol; polyethylene glycol; pluronics; hydroxyalkyl starches, e.g. hydroxyethyl starch (HES), and combinations thereof. Preferably, the lyoprotectants include sugars, such as sucrose or trehalose; amino acids such as monosodium glutamate or histidine; methylamines such as betaine; lyotropic salts such as magnesium sulfate; polyols such as trihydric or higher sugar alcohols, e.g. glycerin, erythritol, glycerol, arabitol, xylitol, sorbitol, and mannitol; ehthylene glycol; propylene glycol; polyethylene glycol; pluronics; hydroxyalkyl starches, e.g. hydroxyethyl starch (HES), and combinations thereof.

The preferred lyoprotectant is a non-reducing sugar, such as trehalose or sucrose, especially trehalose.

The lyoprotectant is preferably added to the composition before the drying step in a "lyoprotecting amount" which means that, following drying of the protein prodrug in the presence of the lyoprotecting amount of the lyoprotectant, the protein prodrug essentially retains its physical and chemical stability and integrity upon drying and storage.

The dry compositions of rhGH polymer prodrug according to the present invention may contain one or more excipients. Excipients used in parenteral compositions may be categorized as, for example, buffering agents, isotonicity modifiers, preservatives, stabilizers, anti-adsorption agents, oxidation protection agents, or other auxiliary agents. However, in some cases, one excipient may have dual or triple functions. The dry composition may contain one or more than one of the following excipients:

(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used. Buffering capacity may be adjusted to match the conditions most sensitive to pH stability (ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum (iii) Preservatives: multidose parenteral preparations require the addition of preservatives at sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride (iv) Stabilizers: Stabilisation is achieved by strengthening of the protein-stabilising forces, by destabilisation of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or LISA may be used (v) Anti-adsorption agents: Mainly ionic or iron-ionic surfactants or other proteins or soluble polymers are used to coat or adsorb competitively to the inner surface of the composition's or composition's container. Eg, poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value (vi) Cryoprotectants: During freeze- or spray drying, excipients may counteract the destabilising effects caused by hydrogen bond breaking and water removal. For this purpose sugars and polyols may be used but corresponding positive effects have also been observed for surfactants, amino acids, non-aqueous solvents, and other peptides. Trehalose is particularly efficient at reducing moisture-induced aggregation and also improves thermal stability potentially caused by exposure of protein hydrophobic groups to water. Mannitol and sucrose may also be used, either as sole lyo/cryoprotectant or in combination with each other where higher ratios of mannitol:sucrose are known to enhance physical stability of a protein in a dry composition. Mannitol may also be combined with trehalose. Trehalose may also be combined with sorbitol or sorbitol used as the sole protectant. Starch or starch derivatives may also be used (vii) Oxidation protection agents: antioxidants such as ascorbic acid, ectoine, methionine, glutathione, monothioglycerol, morin, polyethylenimine (PEI), propyl gallate, vitamin E, chelating agents such as citric acid, EDTA, hexaphosphate, thioglycolic acid (viii) Other auxiliary agents: such as wetting agents, viscosity modifiers, antibiotics. Acids and bases such as hydrochloric acid and sodium hydroxide are auxiliary agents necessary for pH adjustment during manufacture.

In one embodiment of the present invention, the dry composition of rhGH polymer prodrug is provided as a single dose, meaning that the container comprising the dry composition of rhGH polymer prodrug comprises one therapeutic dose.

Thus, in another aspect of the present invention the composition is provided as a single dose composition.

In another embodiment, the dry composition of rhGH polymer prodrug contains multiple doses, meaning that the container comprising the dry composition of rhGH polymer prodrug contains more than one therapeutic dose. Preferably, a multiple dose composition contains at least 2 doses, such as from 2 to 12 doses of hGH polymer prodrug and preferably at least 4 doses.

Thus, in another aspect of the present invention the composition is provided as a multiple dose composition.

In a further aspect, the composition according to the present invention is characterized in that it contains one or more additional biologically active agents, either in its free form or as a prodrug, and wherein the one or more additional biologically active agents are selected from the group consisting of IGF-1, ghrelin or ghrelin-like compounds, gonadotropin releasing hormone agonists and/or analogs, growth hormone releasing factor and analogs, gonadal steroids, antiandrogens, non-steroidal aromatase inhibitors, HIV combination therapy, free fatty acid regulators, anabolic steroids, estrogen agonists/antagonists, propranolol, appetite suppressants osteoporosis drugs including bisphosphonates, bone formation agents, estrogens, parathyroid hormones, and selective receptor modulators, and/or anti-diabetic drugs such as insulin, thiazolidinediones, sulfonyl ureas, incretin memetics, meglitinides, biguanides, alpha-glucosidase inhibitors and amylin analogues. Prodrugs used for additional biologically active agents are preferably also transient polymer prodrugs and especially prodrugs as described herein for rhGH. Preferably, the additional biologically active agents are contained in there free from.

Prior to applying the dry composition of the rhGH polymer prodrug composition to a patient in need thereof, the dry composition is reconstituted. Reconstitution can take place in the container in which the dry composition of rhGH polymer prodrug is provided, such as in a vial, syringe, dual-chamber syringe, ampoule, and cartridge, or the dry composition of rhGH polymer prodrug may be transferred to a different container and is then reconstituted. Reconstitution is done by adding a predefined amount of reconstitution solution to the lyophilisate. The reconstitution solutions are sterile liquids, such as water or buffer, which may contain further additives, such as preservatives and/or antimicrobials. If the rhGH polymer prodrug composition is provided as single dose, the reconstituion solution may contain one or more than one preservative and/or antimicrobial. Preferably, it is sterile water. If the rhGH polymer prodrug composition is a multiple dose composition, it is preferred that the reconstitution solution contains one or more preservative and/or antimicrobial, such as, for example, benzylalcohol and cresol.

The reconstituted composition preferably comprises

| | |
|---|---|
| rhGH polymer prodrug | 10-300 mg/ml |
| succinic acid | 5-50 mM |
| trehalose dihydrate | 25-850 mg/ml, |
| and has a pH ranging from pH 4.5 to pH 6. | |

More preferably, the reconstituted composition comprises

| | |
|---|---|
| rhGH polymer prodrug | 10-300 mg/ml |
| succinic acid | 5-50 mM |
| trehalose dihydrate | 30-150 mg/ml, |
| and has a pH ranging from pH 4.5 to pH 6. | |

Even more preferably, the reconstituted composition comprises

| | |
|---|---|
| rhGH polymer prodrug | 10-300 mg/ml |
| succinic acid | 5-50 mM |
| trehalose dihydrate | 50-100 mg/ml, |
| and has a pH ranging from pH 4.5 to pH 6. | |

Most preferably, the reconstituted composition comprises

| | |
|---|---|
| rhGH polymer prodrug | 30-60 mg/ml |
| succinic acid | 10 mM |
| trehalose dihydrate | 70-85 mg/ml, |
| and has a pH ranging from pH 4.5 to pH 5.5. | |

Optionally, the reconstituted composition comprises one or more preservative and/or antimicrobial.

Optionally, the reconstituted composition comprises one or more excipient.

After reconstitution, a single dose composition of rhGH polymer prodrug has a volume of not more than 4 ml, such as from about 0.5 to about 3.5 ml.

In a reconstituted, multi-dose composition of rhGH polymer prodrug, each dose has a volume of not more than 4 ml, such as from about 0.5 to about 3.5 ml. The individual therapeutic doses of such multiple dose composition of rhGH polymer prodrug can either be used for different patients in need thereof or can be used for one patient, whereas after the application of the first dose the remaining doses are stored until needed. In the latter case, the reconstituted rhGH polymer prodrug is stable for at least 2 weeks, preferably for at least 4 weeks, and more preferably for at least 6 weeks, when stored at 2-8° C.

Preferably, the hGH polymer prodrug is sufficiently dosed in the composition to provide therapeutically effective amount of hGH for at least three days in one application. More preferably, the one application of the hGH polymer prodrug provides therapeutically effective amount of hGH for four days, even more preferably for five days and most preferably for one week.

In another aspect of the present invention the composition is comprised in a container, such as a vial, syringe, dual-chamber syringe, ampoule, and cartridge. Preferably the container is a dual-chamber syringe. Especially the dry composition according to the present invention is provided in a first chamber of the dual-chamber syringe and reconstitution solution is provided in a second chamber of the dual-chamber syringe.

Another aspect of the present invention is a method of manufacturing a composition according to the present invention, comprising the steps of
(i) admixing the rhGH polymer prodrug with one or more lyoprotectants and optionally one or more excipients,
(ii) transferring amounts of the mixture from step (i) equivalent to the desired number of dosages into suitable chambers of a container,
(iii) drying the mixture, and
(iv) sealing the container.

Preferably, the method of manufacturing a composition of the present invention comprises the steps of
(i) admixing the rhGH polymer prodrug with trehalose dihydrate and succinic acid to yield a composition comprising

| rhGH polymer prodrug | 10-300 mg/ml |
|---|---|
| succinic acid | 5-50 mM |
| trehalose dihydrate | 25-850 mg/ml, |

(ii) adjusting the pH of the composition of step (i) to a pH ranging from pH 4.0 to pH 6.5 with tris,
(iii) transferring amounts of the mixture from step (i) equivalent to the desired number of dosages into suitable chambers of a container,
(iv) drying the mixture, and
(v) sealing the container;
whereas the order of steps (ii) and (iii) may be changed.

Preferably, the composition in step (i) comprises

| rhGH polymer prodrug | 10-300 mg/ml |
|---|---|
| succinic acid | 5-50 mM |
| trehalose dihydrate | 50-100 mg/ml. |

More preferably, the composition in step (i) comprises

| rhGH polymer prodrug | 30-60 mg/ml |
|---|---|
| succinic acid | 10 mM |
| trehalose dihydrate | 70-85 mg/ml. |

The number of chambers may depend on the number of dosages. If only one dosage is intended the container may comprise one, two or more chambers.

Preferably, step (iii) is done by lyophilization.

Preferably, in the method described above the container is a dual-chamber syringe having a first chamber with the mixture comprising the hGH polymer prodrug composition, the method further comprising the step of
filling a second chamber with a reconstitution solution before sealing the container.

Another aspect is a kit of parts. In case the administration device is simply a hypodermic syringe then the kit may comprise the syringe, a needle, a vial containing the reconstitution solution, and a vial or ampoule containing the dry hGH polymer prodrug composition for use with the syringe. Optionally, the kit of parts comprises a safety device for the needle which can be used to cap or cover the needle after use to prevent injury.

In more preferred embodiments, the injection device is other than a simple hypodermic syringe and so the separate container is adapted to engage with the injection device such that in use the liquid composition in the container is in fluid connection with the outlet of the injection device. Most preferably, the separate container is a dual-chamber syringe. Examples of administration devices include but are not limited to hypodermic syringes and pen injector devices. Particularly preferred injection devices are the pen injectors in which case the container is a cartridge, preferably a disposable cartridge.

A preferred kit of parts comprises a needle and a container containing the composition according to the present invention and optionally further containing a reconstitution solution, the container being adapted for use with the needle. Preferably, the container is a dual-chamber syringe.

An additional aspect of the present invention relates to the method of administration of a reconstituted rhGH polymer prodrug composition. The rhGH polymer prodrug composition can be administered by methods of injection or infusion, including intradermal, subcutaneous, intramuscular, intravenous, intraosseous, and intraperitoneal.

A further aspect is a method of preparing a reconstituted composition comprising a therapeutically effective amount of a rhGH polymer prodrug, one or more lyoprotectants and optionally one or more pharmaceutically acceptable excipients, wherein the growth hormone is transiently linked to a polymer carrier, the method comprising the step of
Contacting the composition of the present invention with a reconstitution solution.

Another aspect is a reconstituted composition comprising a therapeutically effective amount of a rhGH polymer prodrug, one or more lyoprotectants and optionally one or more pharmaceutically acceptable excipients, wherein the growth hormone is transiently linked to a polymer carrier obtainable by the method above.

In one embodiment of the present invention the dry composition of polymer rhGH prodrug does not only comprise a rhGH polymer prodrug, a lyoprotectant and, optionally, one or more excipients, but also other biologically active moieties, either in their free form or as prodrugs. Such biologically active moieties are, for example:
IGF-1
ghrelin or ghrelin-like compounds,
gonadotropin releasing hormone analog such as, for example, triptorelin or antiandrogen, such as, for example, cyproterone acetate or non-steroidal aromatase inhibitors, such as, for example, letrozole
HIV combination therapy
free fatty acid regulator, e.g. acipimox
anabolic steroid, eg oxandrolone
estrogen agonist/antagonist
propranolol
appetite suppressant, e.g. sibutramine If the dry composition of hGH polymer prodrug of the present invention comprises other biologically active moieties in the form of a prodrug, then it is preferred that said other biologically active moieties are transiently linked to a polymer. It is also preferred that the transient linkage comprises any of the before described linkers.

In an alternative embodiment, the rhGH polymer prodrug composition according to the present invention is combined with a second biologically active compound in such way that the rhGH polymer prodrug is administered to a patient in need thereof first, followed by the administration of the second compound. Alternatively, the rhGH polymer prodrug composition is administered to a patient in need thereof after another compound has been administered to the same patient.

In a preferred embodiment, the composition of dry rhGH polymer prodrug has the following composition (based on the total weight of the composition):

| | |
|---|---|
| rhGH polymer prodrug | 1.1-92.1% (w/w) |
| succinic acid | 0.1-14.4% (w/w) |
| trehalose, optionally as dihydrate | 7.3-98.7% (w/w) |
| tris | 0.01-25.4% (w/w) |

More preferably, the composition of dry rhGH polymer prodrug has the following composition (based on the total weight of the composition):

| | |
|---|---|
| rhGH polymer prodrug | 7.8-85.5% (w/w) |
| succinic acid | 0.1-8.9% (w/w) |
| trehalose, optionally as dihydrate | 13.6-90.3% (w/w) |
| tris | 0.03-15.7% (w/w) |

Most preferably, the composition of dry rhGH polymer prodrug has the following composition (based on the total weight of the composition):

| | |
|---|---|
| rhGH polymer prodrug | 25.3-46.5% (w/w) |
| succinic acid | 0.8-1.2% (w/w) |
| trehalose, optionally as dihydrate | 52.4-72.8% (w/w) |
| tris | 0.4-2.3% (w/w) |

Preferably, the composition of rhGH polymer prodrug as described above is lyophilized. Preferably, it is lyophilized in a first chamber of a dual-chamber syringe, of which second chamber is filled with reconstitution solution. In one embodiment, the reconstitution solution is sterile water containing 0.7-1.1% benzylalcohol, more preferably 0.9% bezylalcohol. In another embodiment, the reconstitution solution contains 0.2-0.4% cresol, more preferably 0.3% cresol. Preferably, the reconstitution solution is sterile water.

Any of the above described compositions of rhGH polymer prodrugs are used for treating or preventing diseases or disorders, which can be treated by rhGH, such as growth hormone deficiency (GHD), adult onset growth hormone deficiency, Turner syndrome, Prader-Willi syndrome, short bowel syndrome, chronic renal insufficiency, small for gestational age (SGA), AIDS wasting, anti-ageing, rheumatoid arthritis, idiopathic small stature, short stature homeobox gene and somatopause. Included is also short stature associated with prolonged steroid use, Aarskog's syndrome, among others.

Also included are chronic renal disease, juvenile rheumatoid arthritis; cystic fibrosis, HIV-infection in children receiving HAART treatment (HIV/HALS children); short stature in children born with very low birth weight (VLBW) but SGA; skeletal dysplasia; hypochondroplasia; achondroplasia; idiopathic short stature (ISS); GHD in adults; fractures in or of long bones, such as tibia, fibula, femur, humerus, radius, ulna, clavicula, matacarpea, matatarsea, and digit; fractures in or of spongious bones, such as the scull, base of hand, and base of foot; patients after tendon or ligament surgery in e.g. hand, knee, or shoulder; distraction oteogenesis; disorders resulting from hip or discus replacement, meniscus repair, spinal fusions or prothesis fixation, such as in the knee, hip, shoulder, elbow, wrist or jaw; disorders resulting from fixing of osteosynthesis material, such as nails, screws and plates; non-union or mal-union of fractures; disorders resulting from osteatomia, e.g. from tibia or $1^{st}$ toe; disorders resulting from graft implantation; articular cartilage degeneration in knee caused by trauma or arthritis; osteoporosis in patients with Turner syndrome; osteoporosis in men; adult patients in chronic dialysis (APCD); manutritional associated cardiovascular disease in APCD; reversal of cachexia in APCD; cancer in APCD; chronic abstractive pulmonal disease in APCD; HIV in APCD; elderly with APCD; chronic liver disease in APCD, fatigue syndrome in APCD; Crohn's disease; impaired liver function; males with HIV infections; short bowel syndrome; central obesity; HIV-associated lipodystrophy syndrome (HALS); male infertility; patients after major elective surgery, alcohol/drug detoxification or neurological trauma; aging; frail elderly; osteo-arthritis; traumatically damaged cartilage; erectile dysfunction; fibromyalgia; memory disorders; depression; traumatic brain injury; subarachnoid haemorrhage; very low birth weight; metabolic syndrome; glucocorticoid myopathy; and short stature due to glucocorticoid treatment in children.

EXAMPLES

Example 1

Synthesis of hGH Polymer Prodrug

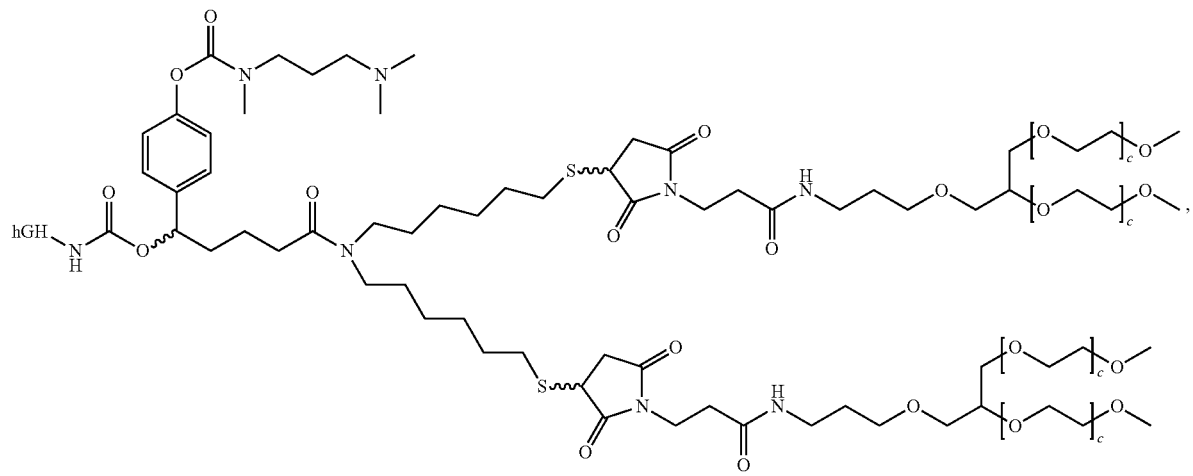

hGH polymer prodrug (1) with c~500 was synthesized as described in WO-A 2009/133137.

Example 2

Stability Testing of Compositions Containing hGH Polymer Prodrug

Five different lyophilized compositions (C1, C2, C3, C4, and C5) of hGH polymer prodrug were prepared. Each composition contained amounts of hGH polymer prodrug 1 to yield a concentration of 5 mg/ml after reconstitution. Formulations were placed upright in an incubator set to 40° C./75% RH. After 17 days, one vial per formulation was removed from the respective incubator, reconstituted with sterile water for injection and subjected to analysis.

| | hGH polymer prodrug (mg/mL) | Buffer | Base | pH | Trehalose (mg/mL) | Mannitol (mg/mL) | Glycine (mg/mL) |
|---|---|---|---|---|---|---|---|
| C1 | 5 | Succinic acid (10 mM) | Tris | 4.0 | 92 | — | — |
| C2 | 5 | Succinic acid (10 mM) | Tris | 4.0 | 10 | 40 | — |
| C3 | 5 | Succinic acid (10 mM) | Tris | 4.0 | — | 46 | 20 |
| C4 | 5 | Succinic acid (10 mM) | Tris | 6.0 | 10 | 40 | — |
| C5 | 5 | Phosphate (5 mM) | Sodium hydroxide | 6.5 | 10 | 40 | — |

| | Visual inspection before/after reconstitution | Free hGH, % of total integrated area for free hGH peak | Peptide mapping (% impurity) isoaspartate | Peptide mapping (% impurity) succinimide | Peptide mapping (% impurity) deamidation | Peptide mapping (% impurity) oxidation |
|---|---|---|---|---|---|---|
| C1 | Intact white cake/clear colorless | 0.15 (t = 0); 0.35 (t = 17d) | 1.89 (t = 0); 3.22 (t = 17d) | 1.75 (t = 0); 2.79 (t = 17d) | 2.0 (t = 0); 1.9 (t = 17d) | 1.25 (t = 0); 1.64 (t = 17d) |
| C2 | Intact white cake/clear colorless | 0.14 (t = 0); 0.51 (t = 17d) | 1.82 (t = 0); 5.68 (t = 17d) | 2.24 (t = 0); 5.08 (t = 17d) | 1.8 (t = 0); 1.8 (t = 17d) | 1.39 (t = 0); 1.65 (t = 17d) |
| C3 | Intact white cake/clear colorless | 0.11 (t = 0); 0.65 (t = 17d) | 1.79 (t = 0); 8.69 (t = 17d) | 2.23 (t = 0); 8.09 (t = 17d) | 2.0 (t = 0); 2.3 (t = 17d) | 1.25 (t = 0); 1.22 (t = 17d) |
| C4 | Intact white cake/clear colorless | 0.39 (t = 0); 1.46 (t = 17d) | 1.59 (t = 0); 2.16 (t = 17d) | 1.90 (t = 0); 2.19 (t = 17d) | 2.6 (t = 0); 2.8 (t = 17d) | 1.16 (t = 0); 1.23 (t = 17d) |
| C5 | Intact white cake/clear colorless | 0.47 (t = 0); 1.04 (t = 17d) | 1.42 (t = 0); 1.94 (t = 17d) | 1.69 (t = 0); 1.71 (t = 17d) | 3.1 (t = 0); 3.2 (t = 17d) | 1.94 (t = 0); 1.90 (t = 17d) |

Example 3

Stability Testing of Compositions Containing hGH Polymer Prodrug

Three different lyophilized compositions (C6, C7, and C8) of hGH polymer prodrug were prepared. Each composition contained amounts of hGH polymer prodrug 1 to yield a concentration of 30 mg/ml after reconstitution. Formulations were placed upright in an incubator set to 40° C./75% RH and an incubator set to 2-8° C., respectively. At each time point, one vial per formulation was removed from the respective incubator, reconstituted with sterile water for injection and subjected to analysis.

| | hGH polymer prodrug (mg/mL) | Buffer | Base | pH | Trehalose (mg/mL) |
|---|---|---|---|---|---|
| C6 | 30 | Succinic acid (10 mM) | Tris | 4.0 | 92 |
| C7 | 30 | Succinic acid (10 mM) | Tris | 5.0 | 92 |
| C8 | 30 | Phosphate (10 mM) | Sodium hydroxide | 6.0 | 92 |

| | Visual inspection before/after reconstitution | Free hGH after n weeks at 40° C./ 75% RH, % of total integrated area for free hGH peak | Free hGH after n weeks at 2-8° C., % of total integrated area for free hGH peak |
|---|---|---|---|
| C6 | Intact white cake/ clear colorless | 0.4 (n = 0); 0.6 (n = 2); 0.7 (n = 4); 0.9 (n = 9) | 0.4 (n = 0); 0.4 (n = 4); 0.4 (n = 9) |
| C7 | Intact white cake/ clear colorless | 0.6 (n = 0); 0.9 (n = 2); 1.0 (n = 4); 1.4 (n = 9) | 0.6 (n = 0); 0.6 (n = 4); 0.6 (n = 9) |
| C8 | Intact white cake/ clear colorless | 0.7 (n = 0); 1.1 (n = 2); 1.2 (n = 4); 1.6 (n = 9) | 0.7 (n = 0); 0.7 (n = 4); 0.7 (n = 9) |

Example 4

Stability Testing of Compositions Containing hGH Polymer Prodrug

A lyophilized composition (C9) of hGH polymer prodrug was prepared. The composition contained amounts of hGH polymer prodrug 1 to yield a concentration of 30 mg/ml after reconstitution. Formulation was placed upright in an incubator set to 40° C./75% RH. After each time point, one vial was removed from the respective incubator, reconstituted with sterile water for injection and subjected to analysis.

|  | hGH polymer prodrug (mg/mL) | Buffer | Base | pH | Trehalose dihydrate (mg/mL) |
|---|---|---|---|---|---|
| C9 at 40° C. | 30 | Succinic acid (10 mM) | Tris | 5.0 | 85 |

|  | Visual inspection before/after reconstitution | Free hGH, % of total integrated area for free hGH, peak after n weeks | Peptide mapping (% impurity) Isoaspartate (after n weeks) | Peptide mapping (% impurity) Succinimide (aftr n weeks) | Peptide mapping (% impurity) Deamidation (after n weeks) | Peptide mapping (% impurity) Oxidation (after n weeks) |
|---|---|---|---|---|---|---|
| C9 at 40° C. | Intact white cake, no cracking around meniscus, no loose pieces, no pull back from vial | 0.6 (n = 0); 0.9 (n = 2); 1.0 (n = 4); 1.4 (n = 9) | 1.8 (n = 2); 2.0 (n = 4); 2.1 (n = 9) | 0.8 (n = 2); 0.9 (n = 4); 1.2 (n = 9) | 4.4 (n = 2); 4.2 (n = 4); 5.3 (n = 9) | 2.1 (n = 2); 3.1 (n = 4); 3.2 (n = 9) |

Example 5

Stability Testing of Compositions Containing hGH Polymer Prodrug

A lyophilized composition (C20) of hGH polymer prodrug was prepared. The composition contained amounts of hGH polymer prodrug 1 to yield a concentration of 30 mg/ml after reconstitution. The formulations were placed upright in an incubator set to 5±3° C. and an incubator set to 25±2° C., respectively. After each time point, one vial was removed from the respective incubator, reconstituted with sterile water for injection and subjected to analysis.

|  | hGH polymer prodrug (mg/mL) | Buffer | Base | Trehalose dihydrate (mg/mL) | pH after n months |
|---|---|---|---|---|---|
| C20 at 5° C. | 30 | Succinic acid (10 mM) | Tris | 85 | 5.1 (n = 0); 5.1 (n = 1); 5.0 (n = 3); 5.0 (n = 4); 5.1 (n = 6); 5.1 (n = 9); 4.9 (n = 12); 5.1 (n = 15); 5.1 (n = 18) |
| C20 at 25° C. | 30 | Succinic acid (10 mM) | Tris | 85 | 5.1 (n = 0); 5.1 (n = 1); 5.1 (n = 3); 5.0 (n = 4); 5.1 (n = 6); 5.0 (n = 9); 5.0 (n = 12); 5.0 (n = 15); 5.0 (n = 18) |

|  | Visual inspection before/after reconstitution | Free hGH, % of total intgrated area for free hGH peak after n months | Peptide mapping (% impurity) isoaspartate after n months | Peptide mapping (% impurity) succinimide after n months | Peptide mapping (% impurity) deamidation after n months | Peptide mapping (% impurity) oxidation after n months |
|---|---|---|---|---|---|---|
| C20 at 5° C. | Intact white cake/clear colorless | 1.4 (n = 0); 1.4 (n = 1); 1.4 (n = 3); 1.4 (n = 4); 1.4 (n = 6); 1.4 (n = 9); 1.5 (n = 12); 1.4 (n = 15); 1.4 (n = 18) | 1.9 (n = 0); 1.9 (n = 1); 1.8 (n = 3); 1.8 (n = 4); 1.9 (n = 6); 1.6 (n = 9); 1.9 (n = 12); 1.8 (n = 15); 1.8 (n = 18) | 0.8 (n = 0); 0.7 (n = 1); 0.8 (n = 3); 0.8 (n = 4); 0.7 (n = 6); 1.9 (n = 9); 1.2 (n = 12); 1.3 (n = 15); 1.4 (n = 18) | 4.0 (n = 0); 4.0 (n = 1); 3.9 (n = 3); 4.0 (n = 4); 4.0 (n = 6); 3.9 (n = 9); 5.1 (n = 12); 3.9 (n = 15); 3.9 (n = 18) | 2.9 (n = 0); 3.4 (n = 1); 2.7 (n = 3); 2.5 (n = 4); 2.5 (n = 6); 2.5 (n = 9); 2.7 (n = 12); 2.7 (n = 15); 2.9 (n = 18) |
| C20 at 25° C. | Intact white cake/clear colorless | 1.4 (n = 0); 1.4 (n = 1); 1.5 (n = 3); 1.5 (n = 4); 1.5 (n = 6); 1.7 (n = 9); 1.7 (n = 12); 1.7 (n = 15); 1.7 (n = 18) | 1.9 (n = 0); 1.9 (n = 1); 1.9 (n = 3); 1.9 (n = 4); 2.0 (n = 6); 1.8 (n = 9); 2.1 (n = 12); 2.1 (n = 15); 2.3 (n = 18) | 0.8 (n = 0); 0.7 (n = 1); 0.8 (n = 3); 0.9 (n = 4); 0.8 (n = 6); 1.0 (n = 9); 1.5 (n = 12); 1.7 (n = 15); 1.6 (n = 18) | 4.0 (n = 0); 4.3 (n = 1); 4.0 (n = 3); 4.0 (n = 4); 3.9 (n = 6); 3.8 (n = 9); 4.8 (n = 12); 3.8 (n = 15); 4.4 (n = 18) | 2.9 (n = 0); 3.3 (n = 1); 3.1 (n = 3); 2.7 (n = 4); 2.7 (n = 6); 2.7 (n = 9); 2.9 (n = 12); 3.1 (n = 15); 3.3 (n = 18) |

Example 6

Stability Testing of Compositions Containing hGH Polymer Prodrug

A lyophilized composition (C10) of hGH polymer prodrug was prepared. The composition contained amounts of hGH polymer prodrug 1 to yield a concentration of 44 mg/ml after reconstitution. The formulations were placed upright in an incubator set to 40±2° C. at a relative humidity of 75±5%. After each time point, one vial was removed from the respective incubator, reconstituted with sterile water for injection and subjected to analysis.

|  | hGH polymer prodrug (mg/mL) | Buffer | Base | pH | Trehalose (mg/mL) |
|---|---|---|---|---|---|
| C10 | 44 | Succinic acid (10 mM) | Tris | 5.0 | 75 |

|  | Visual inspection before/after reconstitution | Free hGH, % of total integrated area for free hGH peak after n weeks | Peptide mapping (% impurity) isoaspartate after n weeks | Peptide mapping (% impurity) succinimide after n weeks | Peptide mapping (% impurity) deamidation after n weeks | Peptide mapping (% impurity) oxidation after n weeks |
|---|---|---|---|---|---|---|
| C10 at 40° C. | Intact white cake, no cracking around meniscus, no loose pieces, no pull back from vial | 0.3 (n = 0); 0.7 (n = 4); 1.1 (n = 8); | 1.7 (n = 0); 2.0 (n = 4); 2.2 (n = 8); | 1.1 (n = 0); 1.2 (n = 4); 1.3 (n = 8); | 4.8 (n = 0); 4.8 (n = 4); 4.8 (n = 8); | 1.9 (n = 0); 2.0 (n = 4); 2.1 (n = 8); |

Example 7

Stability Testing of Compositions Containing hGH Polymer Prodrug

A lyophilized composition (C11) of hGH polymer prodrug was prepared. The composition contained amounts of hGH polymer prodrug 1 to yield a concentration of 52 mg/ml after reconstitution. The formulations were placed upright in an incubator set to 40±2° C. at a relative humidity of 75±5%. After each time point, one vial was removed from the respective incubator, reconstituted with sterile water for injection and subjected to analysis.

|  | hGH polymer prodrug (mg/mL) | Buffer | Base | pH | Trehalose (mg/mL) |
|---|---|---|---|---|---|
| C11 | 52 | Succinic acid (10 mM) | Tris | 5.0 | 74 |

| | Visual inspection before/after reconstitution | Free hGH, % of total integrated area for free hGH peaks after n weeks | Peptide mapping (% impurity) isoaspartate after n weeks | Peptide mapping (% impurity) succinimide after n weeks | Peptide mapping (% impurity) deamidation after n weeks | Peptide mapping (% impurity) oxadiation after n weeks |
|---|---|---|---|---|---|---|
| C11 at 40° C. | Intact white cake, no cracking around meniscus, no loose piece, no pull back from vial | 2.0 (n = 0); 2.6 (n = 4); 2.9 (n = 8); | 1.3 (n = 0); 1.6 (n = 4); 1.7 (n = 8) | 0.8 (n = 0); 1.0 (n = 4); 1.1 (n = 8) | 4.2 (n = 0); 4.2 (n = 4); 3.9 (n = 8) | 1.3 (n = 0); 1.5 (n = 4); 1.8 (n = 8) |

Methods:

Lyophilized compositions: Ultra-/diafiltration or dialysis was employed to obtain a concentrated aqueous solution containing hGH polymer prodrug from column eluate. Buffer exchange against buffer containing succinate or phosphate pH-adjusted by Tris or sodium hydroxide, respectively, and trehalose dihydrate and/or mannitol and/or glycine, was performed to obtain an aqueous buffered solution containing the desired concentration of hGH polymer prodrug, which subsequently was frozen and lyophilized.

RP-HPLC to detect free hGH: Mobile phase A was composed of 0.05% aqueous TFA (e.g. 0.5 mL in 999.5 mL HPLC-grade water) and mobile phase B was composed of 0.04% TFA in acetonitrile (e.g. 0.4 mL TFA in 999.6 mL acetonitrile). A Waters UPLC C18 BEH 300 Å 1.7 µm 2.1×50 mm column was used. Flow rate was set to 0.4 mL/min, detection was at a wavelength of 215 nm, the column running temperature was 30° C. (±5° C.). The sample cooler temperature was set at 4° C. and the sample injection load was 100 µg (10 µL of a 10 mg/mL sample). Samples were transferred to 0.22-µm PVDF centrifugal filters (Millipore, #UFC30GVNB) and filtered by centrifugation for 1 min at 9,000×g. Filtered samples were diluted to 10 mg/ml with formulation buffer.

Tryptic digest of polymeric hGH prodrug and peptide mapping: Tryptic digestion of hGH-conjugates was performed at a trypsin/hGH ratio=1:20 (w/w). The pH was adjusted with proteolysis buffer concentrate to pH=7.0 to minimize the hGH-cleavage from the transient hGH-PEG conjugate during the digest. After 8 h incubation at 37° C. the digest was stopped by the addition of 5% (w/w) phosphoric acid solution. The resulting peptide mixture was separated by RP-HPLC on a C18 column with 300 A pore size and 1.7 µm particle diameter. A gradient combination with 0.05 vol % aq. TFA and 0.04% TFA in acetonitrile as eluents and detection at 215 nm was created. The tryptic fragments which eluted with reasonable resolution were characterized via LC-MS and compared to theoretical monoisotopic masses. The protein sequence coverage was 96% (184 of 191 amino acids).

Impurities were quantified as tryptic peptides based on their respective peak area relative to the peak area of the corresponding unmodified tryptic peptide. Under the conditions of the tryptic digest and subsequent RP-HPLC-MS, both the succinimide intermediate and the isoaspartate could be quantified for ASP130 of the polymeric hGH prodrug.

Under the conditions of the tryptic digest and subsequent RP-HPLC-MS, aspartate formation resulting from ASN149 and ASN152 deamidation could be quantified for the polymeric hGH prodrug.

Under the conditions of the tryptic digest and subsequent RP-HPLC-MS, formation of the sulfoxide degradation product of MET14 could be quantified for the hGH polymer prodrug.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

ABBREVIATIONS

LC-MS—liquid chromatography-coupled mass spectrometry
PVDF—polyvinylidene fluoride
RH—relative humidity
RP-HPLC—reversed phase high performance liquid chromatography
TFA—trifluoroacetic acid
Tris—tris(hydroxymethyl)aminomethane
UPLC—ultra performance liquid chromatography

The invention claimed is:

1. A dry composition comprising:
a therapeutically effective amount of a recombinant human growth hormone ("rhGH") polymer prodrug and one or more lyoprotectants, wherein the rhGH is transiently linked via a reversible linker moiety to a polymer carrier;
wherein the composition is stable for at least 6 months when stored at temperatures ranging from 2 to 25° C., and wherein during such storage less than 5% of the rhGH is released from the rhGH polymer prodrug as free rhGH.

2. The composition according to claim 1;
wherein the composition is dried by lyophilization.

3. The dry composition according to claim 1;
wherein the dry composition is stable for at least 1 year when stored at 2-25° C.

4. The composition according to claim 1;
wherein the lyoprotectant is trehalose.

5. The composition according to claim 1;
wherein the composition is provided as a single dose composition.

6. The composition according to claim 1;
wherein the composition is provided as a multiple dose composition.

7. The composition according to claim 1;
wherein the rhGH polymer prodrug has the chemical structure shown in (A):

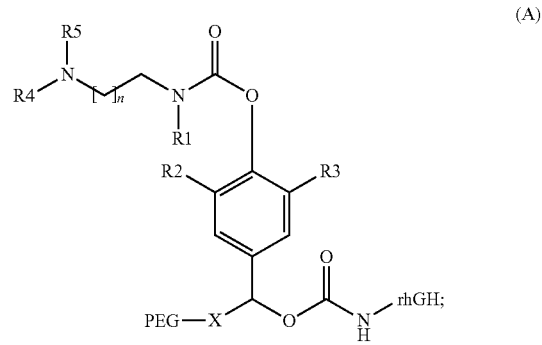

wherein HN-rhGH represents the rhGH residue attached to the reversible linker moiety;
wherein R1, R2, R3, R4, and R5 are selected independently from the group consisting of hydrogen, methyl, ethyl, propyl, isopropyl, butyl, isobutyl, and tertiary butyl;
wherein PEG represents a PEGylation residue attached to the transient linker;
wherein n=1 or 2; and
wherein X is selected from C1 to C8 alkyl or C1 to C12 heteroalkyl.

8. The composition of claim 7;
wherein the moiety

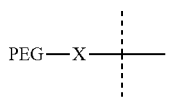

of formula (A) has the following structure:

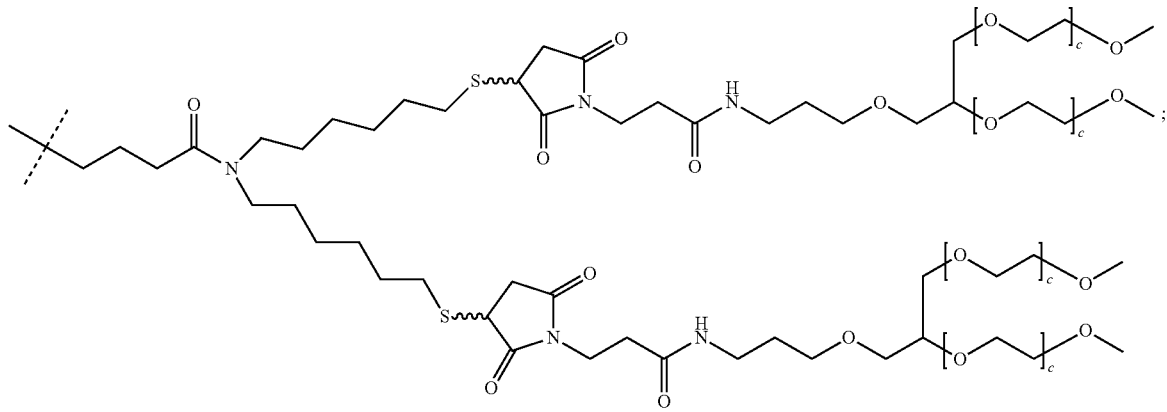

wherein each c is independently an integer from 250 to 750.

9. The composition according to claim 1;
wherein the composition contains one or more additional biologically active agents, either in its free form or as a prodrug, and wherein the one or more additional biologically active agents are selected from the group consisting of:
IGF-1, ghrelin, ghrelin-like compounds, gonadotropin releasing hormone agonists, gonadotropin releasing hormone analogs, growth hormone releasing factor, growth hormone releasing factor analogs, gonadal steroids, antiandrogens, non-steroidal aromatase inhibitors, HIV combination therapy, free fatty acid regulators, anabolic steroids, estrogen agonists, estrogen antagonists, propranolol, appetite suppressants, osteoporosis drugs; and
anti-diabetic drugs.

10. The composition according to claim 1;
wherein the rhGH polymer prodrug is sufficiently dosed in the composition to provide therapeutically effective amount of hGH for at least three days in one application.

11. The composition according to claim 10;
wherein one application of the rhGH polymer prodrug is sufficient for one week.

12. The composition of claim 1;
wherein the composition comprises one or more excipients.

13. The composition of claim 1;
wherein the composition comprises:
rhGH polymer prodrug in an amount of 1.1-92.1% (w/w);
succinic acid in an amount of 0.1-14.4% (w/w);
trehalose, optionally as dihydrate in an amount of 7.3-98.7% (w/w); and
tris in an amount of 0.01-25.4% (w/w).

14. The composition of claim 1;
wherein the composition comprises:
rhGH polymer prodrug in an amount of 7.8-85.5% (w/w);
succinic acid in an amount of 0.1-8.9% (w/w);
trehalose, optionally as dihydrate in an amount of 13.6-90.3% (w/w); and
tris in an amount of 0.03-15.7% (w/w).

15. The composition of claim 1;
wherein the composition comprises:
rhGH polymer prodrug in an amount of 25.3-46.5% (w/w);
succinic acid in an amount of 0.8-1.2% (w/w);
trehalose, optionally as dihydrate in an amount of 52.4-72.8% (w/w); and
tris in an amount of 04-2.3% (w/w).

16. The composition of claim 1;
wherein the rhGH is at least 95% identical to the sequence of SEQ ID NO:1 and at least 30% of all rhGH residues of said composition are PEGylated at position Lys158.

17. The composition according to claim 9;
wherein the osteoporosis drugs are selected from the group consisting of bisphosphonates, bone formation agents, estrogens, parathyroid hormones, and selective receptor modulators.

18. The composition according to claim 9;
wherein the anti-diabetics drugs are selected from the group consisting of insulin, thiazolidinediones, sulfunyl ureas, incretin memetics, meglitinides, biguanides, alpha-glucosidase inhibitors, and amylin analogues.

19. A container comprising the composition of claim 1.

20. The container according to claim 19;
wherein the container is a dual-chamber syringe.

21. The dual-chamber syringe according to claim 20;
the dry composition according to claim 1 is provided in a first chamber of the dual-chamber syringe, and reconstitution solution is provided in a second chamber of the dual-chamber syringe.

22. A kit of parts, comprising:
a needle; and
a container containing the composition according to claim 1;
wherein the container optionally further contains a reconstitution solution; and
wherein the container is configured for use with the needle.

23. The kit of parts according to claim 22;
wherein the container is a dual-chamber syringe.

24. A reconstituted composition comprising:
the composition according to claim 1; and
a reconstitution solution;
wherein the reconstituted composition includes:
   rhGH polymer prodrug in an amount of 10-300 mg/ml;
   succinic acid in an amount of 5-50 mM; and
   trehalose dihydrate in an amount of 25-850 mg/ml; and
wherein the reconstituted composition has a pH ranging from pH 4.5 to pH 6.

25. The reconstituted composition of claim 24;
wherein the reconstituted composition comprises:
   rhGH polymer prodrug in an amount of 10-300 mg/ml;
   succinic acid in an amount of 5-50 mM; and
   trehalose dihydrate in an amount of 30-150 mg/ml;
wherein the reconstituted composition has a pH ranging from pH 4.5 to pH 6.

26. The reconstituted composition of claim 24;
wherein the reconstituted composition comprises:
   rhGH polymer prodrug in an amount of 30-60 mg/ml;
   succinic acid in an amount of 10 mM; and
   trehalose dihydrate in an amount of 70-85 mg/ml; and
wherein the reconstituted composition has a pH ranging from pH 4.5 to pH 5.5.

27. The reconstituted composition of claim 24, further comprising:
one or more preservative and/or antimicrobial.

28. The reconstituted composition of claim 24, further comprising:
one or more excipients.

29. A method of preparing a reconstitution of the composition according to claim 1, the method comprising:
   contacting the composition of claim 1 with a reconstitution solution.

30. A method of manufacturing a composition according to claim 1, the method comprising:
   (i) admixing the rhGH polymer prodrug with one or more lyoprotectants and optionally one or more than one excipients;
   (ii) transferring amounts of the mixture from step (i) equivalent to the desired number of dosages into suitable chambers of a container;
   (iii) drying the mixture; and
   (iv) sealing the container.

31. The method according to claim 30;
wherein step (i) comprises admixing the rhGH polymer prodrug with trehalose dihydrate, and succinic acid to yield a composition comprising:
   rhGH polymer prodrug in an amount of 10-300 mg/ml;
   succinic acid in an amount of 5-50 mM; and
   trehalose dihydrate in an amount of 25-850 mg/ml; and
wherein the method further comprises a pH-adjusting step comprising adjusting the pH of the composition of step (i), either before or after performing step (ii) to a pH ranging from pH 4.0 to pH 6.5 with tris.

32. The method of claim 31,
wherein the composition of step (i) comprises:
   rhGH polymer prodrug in an amount of 10-300 mg/ml;
   succinic acid in an amount of 5-50 mM; and
   trehalose dihydrate in an amount of 30-150 mg/ml.

33. The method of claim 31;
wherein the composition of step (i) comprises:
   rhGH polymer prodrug in an amount of 10-300 mg/ml;
   succinic acid in an amount of 5-50 mM; and
   trehalose dihydrate in an amount of 50-100 mg/ml.

34. The method of claim 31;
wherein the composition of step (i) comprises:
   rhGH polymer prodrug in an amount of 30-60 mg/ml;
   succinic acid in an amount of 10 mM; and
   trehalose dihydrate in an amount of 70-85 mg/nil.

35. The method of claim 31;
wherein in step (ii) the pH is adjusted to a pH ranging from pH 4.5 to pH 5.5.

36. The method according to claim 30;
wherein the container is a dual-chamber syringe having a first chamber with the mixture,
wherein the method further comprises:
   filling a second chamber with a reconstitution solution before sealing the container.

* * * * *